United States Patent [19]

Durette

[11] Patent Number: 4,866,035

[45] Date of Patent: Sep. 12, 1989

[54] DIPEPTIDYL SACCHARIDES AS HOST RESISTANCE ENHANCERS IN AIDS-IMMUNO-COMPROMISED HOSTS AND METHODS OF USE

[75] Inventor: Philippe L. Durette, New Providence, N.J.

[73] Assignee: Merck & Co., Inc., Rahway, N.J.

[21] Appl. No.: 105,056

[22] Filed: Oct. 5, 1987

[51] Int. Cl.$^4$ .................. A61K 37/02; A61K 39/00
[52] U.S. Cl. ............................................. 514/8; 514/9;
514/11; 514/21; 514/42; 514/44; 514/46;
514/50; 514/75; 514/78; 514/357
[58] Field of Search ............... 424/88, 89; 514/8, 11,
514/2, 9, 21, 42, 44, 46, 50, 75, 78, 357; 260/396 R

[56] References Cited

U.S. PATENT DOCUMENTS 4,368,190  1/1983  Shen et al. ........................ 424/88

OTHER PUBLICATIONS

Dagani, "Efforts Intensify to Develop Drugs, Vaccines that Combat AIDS", C & E News, Dec. 8, 1986, pp. 7-14.

Primary Examiner—John Kight
Assistant Examiner—Nathan M. Nutter
Attorney, Agent, or Firm—Robert J. North; John W. Harbour

[57] ABSTRACT

Disclosed are specific dipeptidyl saccharide derivatives which alone, or in combination with an anti-AIDS drug, e.g. azidothymidine, provide protection against opportunistic infection in human individuals whose resistance to infection has been specifically suppressed by an AIDS-related (HIV) virus, as well as help to suppress the AIDS-related infection itself.

4 Claims, No Drawings

DIPEPTIDYL SACCHARIDES AS HOST RESISTANCE ENHANCERS IN AIDS-IMMUNO-COMPROMISED HOSTS AND METHODS OF USE

BACKGROUND OF THE INVENTION

1. Field of the Invention

The present invention relates to dipeptidyl saccharides which, alone, or in combination with an anti-AIDS drug, e.g. azidothymidine, protect against opportunistic infection a human host immunocompromised as a result of n AIDS-related viral infection.

2. Brief Description of Disclosures in the Art

The search for new immunostimulants capable of augmenting host defenses to combat infection, cancer and congenital immunodeficiency disorders is an increasingly important area of pharmaceutical endeavor, particularly as it relates to AIDS related viruses.

Seven years ago few had ever heard of acquired immune deficiency syndrome, or AIDS. This puzzling affliction, then seen in only a small number of young, homosexual men, was something new and unnamed. Today, it's hard to find anyone in the U.S. who hasn't heard of AIDS, the disease that can debilitate and then kill its victim with horrific swiftness.

AIDS has come to be recognized as a public health emergency. More than 27,700 American men, women, and children have been stricken by it; the death toll is 16,000 and rising. The U.S. Public Health Service predicts that by the end of 1991 more than 179,000 persons will have succumbed to the disease.

Thus far, there is no cure for AIDS.

Technically, acquired immune deficiency syndrome (AIDS) is a transmissible deficiency of cellular immunity characterized by opportunistic infections and certain rare malignancies. The dominant risk groups for AIDS include homosexually active males, intravenous drug abusers, recipients of transfusions and blood products, and the heterosexual partners and children of high risk individuals, suggesting the involvement of an infectious agent transmitted through intimate contact or blood products.

Recent evidence indicates that the infectious agent responsible for disease transmission is a novel lymphotropic retrovirus, currently designated HIV I (human immunodeficiency virus) and also known as lymphadenopathy-associated virus (LAV) (Barré-Sinoussi et al., *Science* 220: 868 (1983)). Similar viruses have been reported by other scientific groups (Popovic et al., *Science* 224: 497 (1984); Levy et al. *Science* 25: 840 1984)) and designated human T cell lymphotropic virus type III (HTLV III), AIDS-associated retrovirus (ARV), or immune deficiency associated virus (IDAV). Still more recent data indicates that LAV, HTLV-III, ARV and IDAV share several important characteristics, including substantial nucleotide homology (Wain Hobson et al., *Cell* 40: 9 (1985); Muesing et al., *Nature* 313: 450 (1985); Sanchez-Pescador et al., *Science* 227: 484 (1985)), and should be considered isolates of the same virus, although there is a likelihood that strain to-strain variations among the viral isolates will exist. In addition to exhibiting substantial nucleotide homology, the isolates are similar with respect to morphology, cytopathology, requirements for optimum reverse transcriptase activity, and at least some antigenic properties (Levy, supra: Schupbach et al., *Science* 224: 503 (1984)).

The above materials are hereby incorporated by reference to characterize the phrase "AIDS-related virus".

U.S. Pat. Nos. 4,256,735 and 4,377,570 both to Durette et al. (assigned to Merck & Co., Inc.) describe immunologically active dipeptidyl saccharides and methods of preparation, described herein, which references are both incorporated herein by reference for this particular purpose.

However, the above disclosures do not specifically describe use of the compounds alone, or in combination with an anti-AIDS drug, e.g. azidothymidine, for use as host resistance enhancing agents, i.e., immunostimulators specifically to combat viral, fungal, and bacterial infections in AIDS-immunocompromised hosts.

SUMMARY OF THE INVENTION

In accordance with this invention, there is provided a method of enhancing the host resistance to opportunistic infection in an AIDS-immunocompromised human host comprising the step of administering to said host a composition containing a 2 amino 2-deoxyglycose of the general structural formula 1:

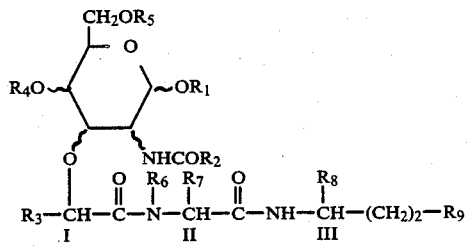

wherein
- $R_1$ is hydrogen, alkyl (1-7C), substituted alkyl (1-7C), phenyl, substituted phenyl, benzyl, or substituted benzyl;
- $R_2$ is alkyl, substituted alkyl, phenyl, or substituted phenyl;
- $R_3$ is H or lower alkyl (1-10C) with the proviso that when the aminoglycose has the 2 amino 2 deoxy-D-glucose configuration, $R_3$ cannot be H;
- $R_4$ and $R_5$ are same or different and are H, aliphatic or aromatic acyl (2-21C) or substituted acyl (2-21C);
- $R_6$ is H, or $R_6$–$R_7$ together is —$CH_2CH_2CH_2$—,
- $R_7$ is H, alkyl (1-7C), hydroxymethyl, mercaptomethyl, benzyl, or substituted benzyl;
- $R_8$ and $R_9$ each is carboxyl, esterified carboxyl (1-7C), amidated carboxyl, or mono- or di alkyl (1-3C) amidated carboxyl; provided that when $R_3$ is lower alkyl, the stereochemistry at asymmetric center I can be either D or L, but that when the aminoglycose has the 2-amino 2-deoxy-D-glucose configuration, the stereochemistry at I cannot be D; and
- when R7 is not H, the stereochemistry at asymmetric center II is either L or D; and
- the stereochemistry at asymmetric center III is D; and pharmaceutically acceptable salts thereof, in a pharmaceutically acceptable carrier therefore, in an amount effective to impart resistance against viral, bacterial, and fungal infection in an AIDS immunocompromised human host.

Also provided is a composition containing the above-described dipeptidyl saccharides in combination with an anti-AIDS drug for enhancing the host resistance in an AIDS immunocompromised human host.

Specifically provided is where the combination composition contains an anti-AIDS drug selected from one or more of the following: azidothmidine, AL 721, ampligen, ansamycin, azimexon, cyclosporine, foscarnet, HPA 23, imreg 1, inosine pranobex, alpha-interferon, interleukin 2, D penicillamine, ribavirin, suramin, CS-85, 2', 3'-dideoxycytidine, 2', 3'-dideoxyadenosine, gamma interferon, RNA deriv, Immune globulin IG-IV, thymopentin, thymostimulin, methionine enkephalin or eguivalents thereof.

Also provided is a method for enhancing resistance against opportunistic infection, being bacterial, viral, or fungal, in a human host immunocompromised by an AIDS related virus comprising administering to said host a pharmaceutical composition, as described above, in which method, the anti-AIDS drug can be administered in combination, concurrently or separately, with the indicated compound.

DETAILED DESCRIPTION OF THE INVENTION AND PREFERRED EMBODIMENTS

The compositions described herein provide very high levels of protection against opportunistic infections in immunocompromised animals and humans.

By the term "AIDS-related virus" is meant the commonly designated HIV series (human immuno deficiency virus) formerly called HTLV and LAV, and species thereof, as described above in the indicated incorporated references.

These compositions may be used prophylactically to protect immunosuppressed animals or patients against infection by opportunistic organisms. In human medicine, the market includes surgery patients, burn victims, cancer patients receiving chemotherapy, aplastic anemics, diabetics, and military recruits. In animal health, the primary potential use markets include major segments of the worldwide economic animal populations during stressful shipping, mixing, and early life adaptation periods.

By the term "immunostimulant", as used herein, is meant a material which can be employed to potentiate a non-specific immune response on the part of the host.

The composition of the present invention does not contain specific antigens per se. Rather, the composition contains only immunostimulants for producing a generalized and nonspecific immunological response on the part of the host, and further includes acceptable salts, carriers, diluents, vehicles and the like for intravenous, subcutaneous or intraperitoneal administration.

The compounds of the above described formula 1 my be prepared by condensing, using conventional procedures, a protected compound of formula 2 with a protected compound of formula 3.

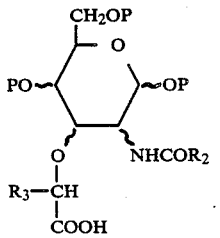

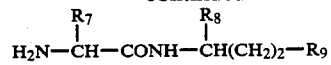

In the foregoing formulas, $R_2$, $R_3$, $R_7$, $R_8$ and $R_9$ represent the groups mentioned previously while P is a protecting group. The protecting group may be any suitable to protect the group to which it is attached during the condensation reaction and which may be readily removed thereafter. As protecting groups for the carboxyl group, there may be mentioned tertiary butyl, benzyl or benzhydryl. For the hydroxyl groups, there may be mentioned the acyl radical, for example, the alkanoyl radical, such as acetyl, the aroyl radical, such as benzoyl, and, in particular, radicals derived from carbonic acid, such as benzyloxycarbonyl or lower alkyloxycarbonyl. Also to be mentioned are alkyl radicals, such as tertiary butyl, benzyl, nitrobenzyl, lower alkoxy radical, or the tetrahydropyranyl radical. In addition, there may be mentioned the optionally substituted alkylidene radicals that block the oxygen atoms at the C-4 and C-6 positions. Among the alkylidene radicals, one finds, in particular, the lower alkylidene radicals, especially ethylidene, isopropylidene, or propylidene, and also, the optionally substituted benzylidene radical, preferentially substituted at the para position. For a more complete listing of protecting groups, reference may be had to standard works on peptide chemistry, e.g. Bodanszky et al., "Peptide Synthesis", chapter 4, Interscience Publishers, 1966 or Schroeder et al., "The Peptides" Vol. I, pp. xxiii–xxix, Academic Press, 1965, and to the text "Protective Groups in Organic Chemistry", Plenum Press, 1973, J. F. W. McOmie,(ed.).

The condensation is effected by reacting the compound 2 in the form where the carboxylic acid is activated with the amino compound 3. The activated carboxyl group may be, for example, an acid anhydride, preferably, a mixed acid anhydride like an acetate of the acid, an amide of the acid like an imidazolid, an isoxazolid or an activated ester. The activated esters, include the cyanomethyl ester, the carboxymethyl ester, the p nitrophenyl thioester, the p-nitrophenyl ester, the 2,4,5-etrichlorophenyl ester, the pentachlorophenyl ester, the N-hydroxysuccinimide ester, the N-hydroxyphthalimide ester, the 8-hydroxyguinoline ester, the 2 hydroxy 1,2 dihydro 1-carboethoxyguinoline esters, the N hydroxypiperidine ester or enol ester derived from N-ethyl 5-phenylisoxazolium 3'-sulfonate. The activated esters may equally be obtained from a carbodiimide by addition of N-hydroxysuccinimide or from a substituted 1 hydroxy benzotriazole for example, a halogen, methyl, or methoxy substituted 3 hydroxy 4 oxo 3,4-dihydrobenzo-[d]-1,2,3 triazine.

The amino group may be activated, for example, by reaction with a phosphitamide.

Among the methods of reaction with the activated esters, one must mention in particular those that involve N ethyl-5-phenyl isoxazolium-3'-sulfonate (Woodward's Reagent K), N ethoxycarbonyl-2-ethoxy-1,2-dihydroguinoline, or carbodiimide. Upon completion of the coupling reaction, the protecting groups may be removed in conventional manner to yield a compound of formula 1.

The starting materials utilized are known or can be made in a known fashion. Thus, one can obtain compounds of formula 2, for example, by reacting the corresponding sugar unsubstituted at position-3 with a halogen $R_3$-acetic acid where $R_3$ has the meaning mentioned above. The ether is obtained in the presence of a strong base. The halogen is preferentially bromo or chloro.

Another process of synthesizing these new glycosamine compounds consists of condensation and eventual deblocking in conventional manner of the protecting groups present in a compound of formula 4.

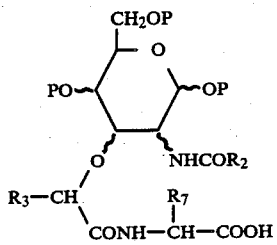

4 wherein $R_2$, $R_3$, and $R_7$ and P have the meaning mentioned above, with a compound of formula 5

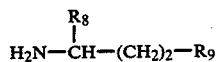

5 wherein $R_8$ and $R_9$ have the meaning mentioned above.

The condensation may be effected by reacting compound 4 in the form of an activated carboxylic acid with the amino compound 5 or by reacting 4 in the form of the free C-terminal carboxyl group with compound 5 where the amino group is present in activated form. The activated carboxyl group can be, for example, an acid anhydride and preferably a mixed acid anhydride, an acid amide or an activated ester. Among these, one finds in particular the acid anhydrides, the amides, or the esters mentioned above. The amino group may be activated, for example, by reaction with a phosphitamide. The readily removable protecting groups correspond to those mentioned above.

The starting materials are obtained in classical fashion. One can, therefore, react the corresponding sugar unsubstituted at position-3-with halogen-$R_3$-acetamido-$R_7$-acetic acid or a compound of formula 2 with an amino-$R_7$-acetic acid where the carboxyl group is blocked as mentioned above followed by removal of the protecting groups to give the compound of formula 1.

Another process for inserting the side chain at position 3 of the sugar radical consists in reacting a compound having structure 6

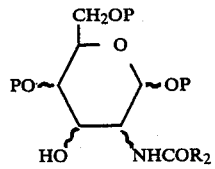

6 where $R_2$ and P have the signification mentioned above with a compound of formula 7

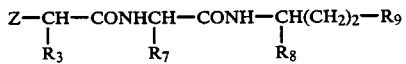

7 where Z represents an esterified hydroxy group capable of reacting and wherein $R_3$, $R_7$, $R_8$ and $R_9$ have the meaning given above followed by removal of the protecting groups optionally present. An esterified hydroxy group capable of reacting is, first of all, a hydroxy group esterified with a strong inorganic or organic acid and especially a group esterified by the hydrohalic acids, like hydrochloric acid, hydrobromic acid, or hydroiodic acid. The protecting groups correspond to those already mentioned above. One can remove them in a classical fashion, for example, by hydrogenolysis with hydrogen in the presence of a noble metal catalyst, such as palladium or platinum, or by acid hydrolysis. The starting materials utilized in this preparative route are known.

One can also obtain the new compounds by acid hydrolysis of the oxazoline and dioxalane rings in the compound of formula 8,

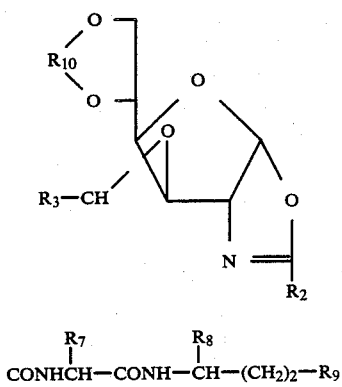

8 where $R_2$, $R_3$, $R_7$, $R_8$ and $R_9$ have the meaning mentioned above and where $R_{10}$ is an alkylidene or cycloalkylidene group, and by removing the protecting groups optionally present.

Alkylidene signifies, particularly in this case, a lower alkylidene, such as isopropylidene and cycloalkylidene, especially cyclopentylidene or cyclohexylidene. This hydrolysis is effected equally in a classical fashion, for example, with acidic ion exchange resins, in particular, with an exchange-resin containing sulfonic acid groups like Amberlite IR 120, (resins of styrene containing strongly acidic sulfonyl groups) or Dowex-50 (polystyrene sulfonic acids) or with a strong inorganic or organic acid like hydrochloric acid, hydrobromic acid, sulfuric acid or a sulfonic acid like methanesulfonic acid or a phenylsulfonic acid optionally substituted in its aromatic nucleus, like p-toluenesulfonic acid, or trifluoroacetic acid.

In the presence of water, one obtains at position-1 a free hydroxy group. In the presence of an alcohol of formula $R_1OH$, where $R_1$ represents an optionally substituted alkyl group, one obtains the corresponding $R_1$ substituted compound. If one of the $R_8$ or $R_9$ carboxyl protecting groups P is the moiety resulting from esterifying the carboxyl group with an alcohol, in particular by a lower alcohol, the alcohol may be hydrolyzed, particularly at high temperature, with aqueous acid to liberate the free acid. During this hydrolysis it is possible that the unsubstituted amino group at position-2 of the molecule of the sugar may be regenerated. One must in this case lastly insert the group

This is achieved in the usual fashion by acylation. In the resulting compounds, the protecting groups may be removed from the peptide radical, for example, by hydrogenolysis, such as with activated hydrogen in a catalytic fashion, or by hydrolysis. The starting materials utilized here are obtained, for example, by inserting the radical $R_3$-acetamidopeptide in one or several steps in the corresponding oxazoline with a free hydroxy group at position-3 of the sugar radical.

In any of the foregoing methods for the synthesis of the compounds of the present invention, when $R_4$ is other than acetyl, the desired group is obtained by employing the appropriate acid anhydride or acid halide, preferably the acid chloride, e.g. propionyl chloride, when $R_4$ is propionyl. When $R_4$ is H and $R_5$ is acyl, it is not necessary to protect $R_4$. However, when $R_5$ is hydrogen and $R_4$ is acyl, then $R_5$ must be protected, preferably as a trityl ether, before acylating $R_4$ followed by deblocking $R_5$. Compounds wherein $R_7$ is other than methyl, may be obtained when, for example, one of the following amino acids is substituted for alanine:

| Amino acid | $R_7$ |
|---|---|
| serine | $CH_2OH$ |
| cysteine | $CH_2SH$ |
| phenylalanine | benzyl |
| tyrosine | p-hydroxybenzyl |
| valine | isopropyl |
| leucine | 2-methylpropyl |
| isoleucine | 1-methylpropyl |
| α-aminobutyric | $CH_2CH_3$ |
| norvaline | $CH_2CH_2CH_3$ |
| norleucine | $CH_2CH_2CH_2CH_3$ |

Compounds wherein $R_6$ and $R_7$ together are $-CH_2CH_2CH_2-$ are obtained by substituting proline for alanine.

The term "substituted alkyl" for $R_1$ and $R_2$ refers to an alkyl group of from 1 to 7 carbon atoms substituted by hydroxy, mercapto, alkoxy of 1-3 carbons, alkyl mercapto of 1 3 carbons, hydroxy or mercapto esterified by an acid of 1-4 carbon atoms, halogen (F, Cl or Br), carboxyl, or carboxyl functionally modified by esterification with a lower alcohol of 1-3 carbons or by amidation. Preferably the alkyl substituents are hydroxy or mercapto, either free or substituted by an alkyl group of 1-3 carbons.

The substituents in the terms "substituted phenyl" for $R_1$ and $R_2$ or "substituted benzyl" for $R_1$ refer to the phenyl group substituted by one or more alkyl groups of 1-3 carbon carbons or hydroxy or mercapto groups either free, or etherified by an alkyl group of 1-3 carbons or esterified by an acid of 1-4 carbons, lower (1-4C) alkyldioxy, cycloalkyldioxy of 5-7 carbon atoms, amino or trifluoromethyl.

Compounds wherein $R_1$ is hydrogen and $R_2$ is other than methyl are obtained by reacting the appropriate 2-amino-2-deoxy-D-glycose, in the case where $R_2$ is alkyl or substituted-alkyl, with the appropriate alkanoic anhydride or alkanoyl halide, preferably chloride, or substituted alkanoic anhydride or substituted-alkanoyl halide, preferably chloride, and in the case where $R_2$ is phenyl or substituted phenyl, with the appropriate aroic anhydride or aroyl halide, preferably chloride, or substituted aroic anhydride or substituted aroyl halide, preferably chloride, in the presence of an appropriate acid acceptor, such as pyridine or triethylamine. The protecting groups P are then introduced at the C-1, C-4, and C-6 positions to give a compound of formula 6 which may then be converted to a compound of formula 2 or formula 4.

In general, compounds wherein $R_1$ is other than hydrogen are prepared by reacting an alcohol of formula $R_1OH$ with the N-alkanoylglycosamine or N-aroylglycosamine to give the corresponding alkyl, substituted alkyl, phenyl, substituted phenyl, benzyl, or substituted benzyl glycopyranoside. The latter are then treated to block the C-4 and C-6 hydroxyl groups, for example, as benzylidene acetal, by reaction with benzylaldehyde and boron trifluoride etherate or zinc chloride. The blocked $R_3$-acetam idodipeptide fragment is then inserted into the blocked glycopyranoside having a free hydroxyl group at position-3 of the sugar radical in one or several steps as described above. The protecting groups are then removed by hydrogenolysis with hydrogen in the presence of a noble metal catalyst, or by acid hydrolysis.

The acyl group for $R_4$ and $R_5$ represents an alkanoyl radical and especially an alkanoyl comprising 2 to 21 carbon atoms, like acetyl or propionyl, and also an aroyl like benzoyl, naphthoyl-1 and naphthoyl 2, and, in particular, benzoyl or naphthoyl substituted with halogen, lower alkyl (1-3C), lower alkoxy (1-3C), trifluoromethyl, hydroxy, or lower alkanoyloxy. Acyl also represents a sulfonyl radical of an organic sulfonic acid like alkanesulfonic acid, in particular, a lower alkanesulfonic acid, like methanesulfonic acid or ethanesulfonic acid or an arylsulfonic acid, in particular, a phenylsulfonic acid optionally substituted by a lower alkyl, like benzenesulfonic acid or toluenesulfonic acid. Acyl also represents a carbamoyl radical, like a non substituted carbamoyl, a lower (1 3C) alkylcarbamoyl or arylcarbamoyl, like the methylcarbamoyl or the phenylcarbamoyl.

For $R_8$ and $R_9$, among the optionally esterified carboxyl groups can be mentioned the carboxyl group esterified by a lower alcohol of 1-3 carbons, like methanol or ethanol. The carboxyl group can also be amidated, unsubstituted at the nitrogen atom or mono or di-substituted with an alkyl, in particular, a lower alkyl, an aryl, particularly phenyl, or an aralkyl, particularly benzyl.

Most preferably, $R_1$ is H, alkyl of 1-3 carbons, benzyl, phenyl or phenyl p substituted by alkyl (1-3C), amino, halogen, hydroxy or trifluoro methyl; $R_2$ is alkyl of 1-3 carbons, or phenyl, or phenyl p substituted by alkyl (1-3C), amino, halogen, hydroxy or trifluoromethyl, $R_3$ is H or lower alkyl of 1-3 carbons, $R_4$ and $R_5$ are H, alkanoyl of 2-21 carbons, benzoyl or naphthoyl, $R_7$ is H, alkyl of 1-4 carbons, hydroxymethyl, mercaptomethyl, benzyl or p-hydroxybenzyl, $R_6$ and $R_7$ together are $-CH_2CH_2CH_2-$, and $R_8$ and $R_9$ are carboxyl, carboxyl esterified by an alcohol of 1-4 carbons, carboxamide, or monoalkyl or dialkyl substituted carboxamide wherein the alkyl group has from 1-3 carbons.

The obtained compounds can be transformed to their salts in a classical fashion, for example, by reacting the acidic compounds obtained with alkaline or alkaline earth hydroxides, or the basic compounds with acids.

The Formula I compounds can be used in the form of salts derived from inorganic or organic acids. Included among such salts are the following: acetate, adipate, alginate, aspartate, benzoate, benzene sulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, succinate, tartate, thiocyanate, tosylate, and undecanoate. Also, the basic nitrogen containing groups can be quaternized with such agents as lower alkyl halides, such as methyl, ethyl, propyl, and butyl chlorides, bromides and iodides; dialkyl sulfates like dimethyl, diethyl, dibutyl, and diamyl sulfates; long chain halides such as decyl, lauryl, myrisyyl and stearyl chlorides, bromides and iodides; aralkyl halides like benzyl and phenethyl bromides and others. Water or oil-soluble or dispersible products are thereby obtained.

The pharmaceutically acceptable compositions of the present invention can be used, for example, for the manufacture of pharmaceutical preparations that contain a pharmaceutically effective amount, for example an amount sufficient for immunostimulation, of the active ingredient together or in admixture with a significant amount of inorganic or organic, solid or liquid pharmaceutically acceptable carriers.

The pharmaceutical preparations according to the invention are for enteral, such as oral or rectal, and parenteral, such as intraperitoneal, intramuscular or intravenous, administration to warm-blooded animals and contain the pharmacologically active ingredient alone or together with a pharmaceutically acceptable carrier.

The carriers may be inorganic or organic and solid or liquid. For example, there are used tablets or gelatine capsules that contain the active ingredient together with diluents, for example lactose, dextrose, sucrose, mannitol, sorbitol, cellulose and/or glycerine, and/or lubricants, for example silica, talc, stearic acid or salts thereof, such as magnesium or calcium stearate, and/or polyethylene glycol. Tablets may also contain binders, for example magnesium aluminum silicate, starches, such as corn, wheat or rice starch, gelatine, methylcellulose, sodium carboxymethylcellulose and/or polyvinylpyrrolidone, and, if desired, disintegrators, for example starches, agar, alginic acid or a salt thereof, such as sodium alginate, and/or effervescent mixtures, or adsorbents, colorings, flavorings and sweeteners. The pharmacologically active compositions of the present invention can also be used in the form of parenterally administrable preparations or in the form of infusion solutions. Such solutions are preferably isotonic aqueous solutions or suspensions, it being possible, for example in the case of lyophilized preparations that contain the active ingredient alone or together with a carrier, for example mannitol, for these to be manufactured before use. The mentioned solutions or suspensions may contain viscosity-increasing substances, such as sodium carboxymethylcellulose, carboxymethylcellulose, dextran, polyvinylpyrrolidone or gelatine. The pharmaceutical preparations may be sterilized and/or contain adjuncts, for example preservatives, stabilizers, wetting agents and/or emulsifiers, solubilizers, salts for regulating the osmotic pressure and/or buffers. The present pharmaceutical preparations which, if desired, may contain other pharmacologically active ingredients, such as antibiotics, are manufactured in a manner known per se, for example by means of conventional mixing, granulating, confectioning, dissolving or lyophilizing processes, and contain approximately from 0.001% to 99%, especially from approximately 0.01% to approximately 10%, more especially from 0.1% to 5%, of the active ingredient(s), an active ingredient concentration of less than 1% being especially suitable for preparations that are to be applied topically.

Pharmaceutical preparations according to the invention may be, for example, in dosage unit form, such as dragees, tablets, capsules, suppositories or ampoules.

Pharmaceutical preparations for oral administration can be obtained by combining the active ingredient with solid carriers, optionally granulating a resulting mixture and processing the mixture or granulate, if desired or necessary after the addition of suitable adjuncts, to form tablets or dragee cores. It is also possible to incorporate them into synthetic carriers that release the active ingredients, or allow them to diffuse, in a controlled manner.

The manufacture of injection preparations is carried out in customary manner under antimicrobial conditions, as is the filling into ampoules or vials and the sealing of the containers.

The compounds described in the present invention also provide, alone, or in combination with "anti AIDS drugs", human host protection against opportunistic infections in individuals immunocompromised by an AIDS related infectious organisms, n addition to direct therapeutic effect against the AIDS related virus. These include fungal, viral and bacterial, including the specific conditions of Kaposi's sarcoma and pneumocystis pneumonia. They are also capable of potentiating antibiotic activity.

By the term "anti AIDS drugs" is meant therapeutic drugs which are thought to act directly or indirectly against the AIDS related virus by a variety of known or unknown mechanisms.

The following anti-AIDS drugs are currently being investigated and are known to exhibit either some antiviral or immunomodulatory effect in a human host against the AIDS related virus (from *Chemical & Engineering News,* Dec. 8, 1986, pp 7-14, hereby incorporated by reference for this purpose):

AL 721. Lipid mixture composed of neutral glycerides, phosphatidylcholine, and phosphatidylethanolamine in 7:2:1 ratio. Interferes with HIV infectivity but not by inhibiting reverse transcriptase; possibly it disrupts the virus's membrane. No adverse effects observed during a six-week clinical trial.

Ampligen. Mismatched double stranded RNA polynucleotide that induces the body to release interferon, thus stimulating antiviral activity. Reportedly does not have side effects of interferon injections. Currently undergoing preliminary clinical trials in AIDS patients.

Ansamycin (rifabutin, $C_{45}H_{29}N_4O_{11}$). Italian antibacterial drug, a member of the rifamycin group of antibiotics, which are characterized by a natural ansa structure (chromophoric naphthohydro quinone group spanned by a long aliphatic bridge). Drug has shown some efficacy in treating AIDS patients with an opportunistic infection caused by the bacterium *Mycobacterium aviumintracellulare.*

Azidothymidine (AZT, 3'-azido 3'-deoxythymidine, zidovudine). First drug to show promise in prolonging lives of patients with AIDS or AIDS-related complex (ARC). Well absorbed orally and effectively penetrates central nervous system, but has relatively short half life in the body and some toxicity, with anemia and headaches. ARC patients treated with AZT showed virtually no toxic effects.

Azimexon. Cyanaziridinyl immunemodulator. Early trial showed improvements in symptoms and immune function in patients with ARC but not AIDS; only toxic effect was mild hemolysis (disintegration of red blood cells with release of hemoglobin), which disappeared when treatment ceased.

Cyclosporine (cyclosporin A). Cyclic undecapeptide with potent immunosuppressive effects, used in cancer therapy. Inhibits T4 lymphocyte dependent immune responses. Basis of controversial AIDS therapy in France; rationale is that HIV infects "activated" T4 cells, which are primed to defend the body, so drug that prevents activation of T4 cells may limit progression of disease. The French claim encouraging results with it.

Foscarnet (trioodium phosphonoformate). Swedish drug that has been used to treat CMV infection in immunocompromised patients, also to treat herpes. Inhibits HIV reverse transcriptase activity in vitro at levels pharmacologically acceptable in vivo. Formulation problems and serious side effects have been encountered. No results yet reported in HIV infected patients.

HPA-23 (ammonium-21-tungsto-9-antimoniate, [(NH$_4$)$_{18}$(NaW$_{21}$Sb$_9$O$_{86}$)$_{17}$]. Inhibits reverse transcriptase in several retroviruses in vitro, but mechanism of antiviral action against HIV is unknown. Drug has shown some tendency to check the growth of HIV, but no therapeutic benefit has been documented in AIDS patients.

Imreg 1. Proprietary immunemodulator derived from white blood cells. Reportedly can enhance production of other biological response modifiers such as interleukin-2 and γ-interferon, which are critical to normal functioning of immune system.

Inosine pranobex (isoprinosine, inosiplex). p-Acetamidobenzoic acid salt of (1 dimethyl amino 2-propanol:inosinate complex 3:3:1 molar ratio). Chemically synthesized antiviral and immune modulator originally developed to enhance memory in elderly. In one study, found to improve immune function in ARC patients.

α-Interferon. Glycoprotein produced by cells in responose to virus infection; helps amplify or regulate immune responses. Checks the growth of HIV in vitro. Has induced tumor regression in some AIDS-related Kaposi's sarcoma cases. Not known whether α-interferon has anti-HIV activity in vivo.

Interleukin 2 (IL 2). Protein made by white blood cells that mediates production of interferon. Inability to produce IL 2 may predispose AIDS patients to opportunistic infections. Preliminary results of therapy with recombinant IL 2 not encouraging, but trials continue.

D-Penicillamine (3-mercapto D-valine). Used to treat rheumatoid arthritis and Wilson's disease, a rare copper-storage disease. Inhibits HIV reproduction in humans. In trials at George Washington University Medical Center, it suppressed the virus but also temporarily depressed T cell levels in 13 AIDS patients with perpetually swollen glands.

Ribavirin (1-β-D-ribofuranosyl-1,2,4-triazole 3-carboxamide). Synthetic nucleoside used to treat a viral respiratory infection in children. In early clinical trials, it inhibited viral replication and improved immune function in AIDS patients. Longer (24-week) trial in 373 ARC patients has been completed; at 12 weeks, ribavirin's safety profile was judged to be acceptable, and the drug was found to be well tolerated.

Suramin (C$_{51}$H$_{34}$Na$_6$O$_{23}$S$_6$). Antiparasitic agent. Potent inhibitor of HIV reverse transcriptase, but also significantly inhibits desirable biological functions. In AIDS patients, it has produced little or no evidence of clinical improvement or immunologic recovery. Has serious side effects, inability to penetrate central nervous system. Not considered appropriate for single-agent use in AIDS. No longer being actively pursued.

Furthermore, the US Food and Drug Administration has released a list of 16 proposed AIDS treatments which have received IND status. The list contains only treatments which "have been publicly acknowledged by their sponsors", and therefore some experimental treatments may have been omitted.

| Experimental treatment | Sponsor |
| --- | --- |
| Immunomodulators | |
| Thymopentin | Ortho Pharmaceuticals |
| Thymostimulin | Serono Laboratories |
| Methionine-enkephalin | National Jewish Hospital |
| Isoprinosine | Newport Pharmaceuticals |
| Antivirals | |
| Ansamycin | Adria Laboratories |
| Ribavirin | Viratek/ICN Pharmaceuticals |
| Dideoxycytidine (DDC) | National Cancer Institute |
| HPA-23 | Rhone-Poulenc |
| AL-721 | Matrix Laboratories[1] |
| Foscarnet | National Institute of Allergy and Infectious Diseases |
| Biologicals | |
| Alpha-interferon | Hoffmann-La Roche |
| Gamma-interferon | Genentech |
| Imreg-1 | Imreg Inc |
| Interleukin-2 | Hoffmann-La Roche |
| RNA deriv | HEM Research |
| Immune globulin IG-IV | Sandoz Pharmaceuticals and Alpha Therapeutics |

Further, Yakult's immunostimulatn, LC-9018, and two herbal products, shosaikoto and ginseng, being studied by Tsumura Juntendo, may be of benefit in patients with AIDS.

LC-9018 has been found to be about 20 times more potent then Ajinomoto's lentinan in inducing macrophage activation, and it is undergoing clinical trials in AIDS patients in the US. Phase III trials with LC-9018 in patients with cancer are currently underway in Japan. Shosaikoto and ginseng have been found to increase depleted helper T cell counts in seven of nine AIDS carriers studied by researchers at Tsumura Juntendo and Tokyo Medical University.

Furthermore, HEM Research's potential anticancer agent, ampligen (a mismatched double-stranded RNA), reduces at least five fold the concentration of Wellcome's azidothymidine (Retrovir) required for inhibitory activity against human immunodeficiency virus (HIV) in vitro, (*The Lancet,* April 18th, p. 890). Ampligen is currently in Phase II clinical trials as an anticancer agent and HEM is seeking partners to fund a clinical trial in AIDS.

At higher concentrations of azidothymidine, there seemed to be a synergistic relation between the two compounds, since complete protection was provided by combined suboptimal doses of each drug. Ampligen could reduce the dose of azidothymidine required for a therapeutic effect in vivo, so educing its toxicity.

Since the two drugs have entirely different modes of action, it is unlikely that they will exert toxicities other than those associated with each drug alone. In recent clinical studies, "virtually no toxicity" was associated with intravenous ampligen. Moreover, since ampligen has clinically demonstrated immunological as well as antiviral activity, its use together with azidothymidine may have pronounced and long term beneficial effects on the course of AIDS beyond that which can be estimated in vitro.

In addition, CS-85, or 3'-azido 2',3' dideoxy 5 ethyl-(uridine), developed by Raymond F. Schinozi at the Veterans Administration Medical Center and Emory University, both in Atlanta, Georgia, shows promise.

All of the above described compounds are deemed to be included within the scope of the term "anti-AIDS drug" as used herein. Use of more than one of these compounds, in addition to the glycopeptide of structure 1, in the combination composition is contemplated.

The composition containing the glycopeptide compounds and an above described anti AIDS drug will contain the glycopeptide in an amount as described above and the anti AIDS drug in an amount, based on the glycopeptide, in a weight ratio of 1:3 to 3:1 and preferably 1:1 based on the weight of glycopeptide.

The dosage form of the combination drug will be 1 to 50 mg/kg of human body weight per day and preferably 2.5 to 40 mg/kg.

The method of co-administering the two ingredients, if not using the combination composition, can be separately, concurrently or simultaneously.

The obtained compounds can be transformed to their salts in a classical fashion, for example, by reacting the acidic compounds obtained with alkaline or alkaline earth hydroxides, or the basic compounds with acids.

The present invention is also directed to pharmaceutical preparations that contain a compound of Formula 1. Among the pharmaceutical preparations relevant to this invention are salts that are administered by external route, for example, orally, rectally or parenterally to human species. Preparations may be administered that contain the pharmacologically active compound by itself or mixed with a pharmacologically acceptable carrier. The dose of the pharmacologically active compound depends on the sex, the age, and the state of the human individual and the mode of application.

The new pharmaceutical preparations contain from about 10% to about 95% and, preferably from about 20% to about 90% of a compound of the present invention. The pharmaceutical preparation relevant to this invention can be presented, for example, in the form of unit doses like tablets, capsules, suppositories, and ampoules.

Also a subject of the invention is a method for administering to an immunocompromised host a composition as described herein, containing a compound of the formula 1, as described, contained in a suitable carrier which may or may not have additional material such as diluents and other materials which may be deemed necessary under the circumstances. However, it is understood that the immunostimulatory preparation does not in fact include a specific antigen as a composition component.

The immunostimulatory properties of the compounds in the present invention can be demonstrate with the following protocols:

1 In vivo Stimulation of Humoral Response: Increase in the Production of Antibodies Against Bovine Serum Albumin (BSA) in the Mouse Mice (NMRI) are immunized by i.p. injections of 10 mg of BSA without precipitate. At 0, 9, 15 and 29 days later blood samples are taken and analyzed for anti-BSA-antibody titers by the passive hemagglutination technique. At the dose utilized, soluble BSA is subimmunogenic for the receiving animals, that is, it does not cause any antibody production, or at most a completely insignificant production. Additional treatment of the mice with certain immunostimulants before or after administration of antigen leads to an increase in antibody titer in the serum. The effect of the treatment is expressed by the obtained score, that is, the sum of the logs to the base 2 of the differences of the titer at 3 days of bleeding.

The compounds disclosed in the present invention are capable of augmenting in a significant manner the production of anti-BSA antibodies by i.p. or sub cutaneous application (s.c.) of 100-300 mg/kg/animal during 5 consecutive days (day 0 to day 4) after immunization with BSA.

The immunostimulatory effect of the compounds mentioned herein depend on the antigen, contrary to other bacterial immunostimulants (like LPS of $E.\ coli$). The injection of the compounds of the present invention results in augmentation of anti-BSA antibody titer only in mice immunized with BSA, and not with non-immunized mice. Subcutaneous administration is as efficacious as i.p., that is, the immunostimulatory effect observed is systemic and does not depend on the fact that the stimulant was administered by the same route as the antigen or mixed with it, as is the case with classical adjuvants.

The compounds disclosed in the present invention permit specific augmentation of humoral immunity, improve immune response, and provide long-lasting immunostimulatory effects on systemic activation of immune apparatus.

2. Stimulation of Mitotic Responses of Lymphocyte Cultures

Mouse lymphoid cells are cultured in microtiter plates, in RPMI 1640 medium with 2% fetal calf serum. Cultures are set in triplicates and consist of $3-5\times10^5$ spleen or $1.5\times10^6$ thymus cells per well in a final volume of 0.2 ml. Class specific mitogens are added at optimal or suboptimal concentrations, while control cultures are incubated without mitogens. The tested compounds are added shortly after the mitogens and the cultures are incubated for 48 hours at 37° with 5% $CO_2$. Incorporation of tritiated thymidine is determined after a pulse (1.0 $\mu$Ci/well) during the last 6 hours in culture. The data are recorded as mean cpm and the effects of the compounds are presented as stimulation index (mean cpm in cultures with the compound/mean cpm in control).

The compounds disclosed in the present invention enhance the levels of thymidine incorporation in lymphocyte cultures, with or without mitogens. The stimulation indices are maximal in control cultures or in those with suboptimal doses of mitogens. Similar effects of the compound are provoked in cultures of different lymphocyte populations, namely, B cells (nude spleen), T cells (thymus) or their mixtures (normal spleen). The effects of the compounds are dose dependent. These compounds, therefore, are capable of stimulating proliferation of lymphocytes that participate in the humoral response (B cells) as well as in cellular immunity (T cells).

3 Compatibility

Although the compounds disclosed in the present invention produce their stimulatory effect with guinea pigs, for example, beginning with a single dose of 0.05 mg/kg s.c., and with mice after 5 applications of 10 mg/kg s.c., no toxic effect is observed after 5 applications of 300 mg/kg i.p., with the mouse. These compounds possess, therefore, a remarkable therapeutic index.

The compounds disclosed in the present invention thus have the capacity, by systemic application, of increasing the immunological reactivity of the treated organism. Moreover, these compounds can enhance cellular as well as humoral immunity and activate lymphocytes responsible for the formation of antibodies.

The compounds disclosed in the present invention can consequently be employed as protective agents against infections caused by bacteria, viruses or pathogenic parasites, owing to immunity by humoral antibodies and/or to cellular mediation. These compounds are therefore especially indicated for stimulation of individual immune defense, e.g., at the time of chronic or acute infections or in cases of selective (antigen specific) immunological deficiencies as well as in situations of immune deficiency, but also acquired general deficiency (i.e., not antigen specific) as appears with age, during initial shock from a grave illness, and before and soon after radiation therapy or immunosuppressive hormones. The said compounds can subsequently be administered in combination with anti-infectious antibiotics, chemical therapeutics or other methods of treatment, to combat immunological deficiencies. The described compounds are thus indicated equally for general prophylaxis of infectious disease in man and animal.

The following examples exhibit the subject invention as contemplated by us and should not be construed as being limiting with respect to the scope and nature of the instant invention.

All temperatures are expressed in degrees Celsius.

EXAMPLE 1

Preparation of 2-Acetamido-2-deoxy-3-O-(D-2-propionyl-L-alanyl-D-isoglutamine)-D-galactose Step A: Preparation of Benzyl 2 acetamido 4,6-O-benzylidene-2-deoxy-3-O-(D-2-propionyl-L-alanyl-D-isoglutamine benzyl ester)-α-D-galactopyranoside A solution of benzyl 2-acetamido 4,6-O-benzylidene-3-O-(D-1-carboxyethyl)-2-deoxy-α-D-galactopyranoside [prepared by the process set forth in P. Sinay and R. W. Jeanloz, *Carbohyd. Res.* 10, 189 (1969)](343.2 mg) in freshly distilled tetrahydrofuran (10 ml) is cooled to 0° and treated with stirring with N hydroxysuccinimide (B4.3 mg) and N,N'-dicyclohexylcarbodiimide (152.4 mg). The reaction mixture is stirred at 0° for 3 hours and then at room temperature for 1 hour. The solids formed are filtered off and washed with tetrahydrofuran. The combined filtrates are cooled to 0° and treated with L-alanyl-D-isoglutamine benzyl ester hydrochloride (253.3 mg) and triethylamine (0.11 ml). The reaction mixture is allowed to attain room temperature and then stirred overnight. After evaporation of the solvent, the solid residue is triturated with water, filtered, taken up in N,N-dimethylformamide and adsorbed onto silica gel (2.5 g) The mixture is applied to a column of silica gel (70 g) and eluted with 33:1 chloroformmethanol. The fractions containing the desired product are combined and concentrated to afford benzyl 2-acetamido-4,6-O-benzylidene-2-deoxy-3O-(D-2-propionyl-L-alanyl-D-isoglutamine benzyl ester)-α-D-galactopyranoside as a white crystalline solid, yield 375.2 mg (68%), m.p. 250°–251°, $[\alpha]_D$ +129° (c 1.0, N,N-dimethylformamide).

Step B: Preparation of 2-Acetamido-2-deoxy-3-O-(D-2-propionyl-L-alanyl-D-isoglutamine)-D-galactose A solution of benzyl 2-acetamido 4,6-O-benzylidene 2-deoxy-3-O-(D-2-propionyl-L-alanyl-D-isoglutamine benzyl ester)-α-D-galactopyranoside (250.3 mg) in glacial acetic acid (10 ml) is hydrogenolyzed in the presence of palladium black at room temperature overnight. The reaction mixture is filtered through Celite, the filtrate evaporated, and traces of acetic acid removed by several coevaporations with toluene. The residue is taken up in the minimal volume of methanol and applied to a column of silica gel and eluted with 80:20:2 $CHCl_3$-$MeOH$-$H_2O$ and subsequently with 60:40:10 $CHCl_3$-$MeOH$-$H_2O$. The fractions containing the desired product are combined, concentrated, the residue taken up in water and lyophilized to afford 2-acetamido 2-deoxy-3O-(D-2-propionyl-L-alanyl-D-isoglutamine)-D-galactose as a white amorphous solid; yield 73 mg (45%); $[\alpha]_D$+44° (c 0.4, water).

EXAMPLE 2

Preparation of 2-Acetamido-2-deoxy 3-O-(D-2-propionyl-L-alanyl-D-isoglutamine)-D-mannose Step A: Benzyl 2-Acetamido-4,6-O-benzylidene-3-O-(D-1-carboxyethyl)-2-deoxy-α-D-mannopyranoside To a stirred solution of benzyl 2-acetamido-4,6-O-benzylidene-2-deoxy-α-D-mannopyranoside [prepared by the process set forth in J. Yoshimura, H. Sakai, N. Oda, and H. Hashimoto, *Bull. Chem. Soc. Japan*, 45, 2027 (1972)] (0.44 g) in dry dioxane (30 ml) at 95° is added sodium hydride (0.25 g) (50% oil suspension) After 1 hour, the temperature is lowered to 65° and then a solution of L-2-chloropropionic acid (0.26 g) in a small volume of dioxane is added After 1 hour, an additional 1 g of sodium hydride is added, and heating with stirring at 65° is continued overnight. Water (15 ml) is carefully added to the cooled reaction mixture. A dark colored lower layer which developed is discarded, and the upper layer is filtered, partially concentrated, and diluted with water (10 ml). The aqueous mixture is extracted with diethyl ether, and the aqueous layer acidified to pH 3 at 0° and extracted with chloroform (3x). The combined organic extracts are dried over anhydrous sodium sulfate and evaporated to give benzyl 2-acetamido-4,6-O-benzylidene-3-O-(D-1-carboxyethyl)-2-deoxy-α-D-mannopyranoside; yield 313 mg.

The 300 MHz nmr spectrum in methanol-d$_4$ is in accord with the desired structure.

Step B: Preparation of Benzyl 2-acetamido-4,6-O-benzylidene-2-deoxy-3-O-(D-2-propionyl-L-alanyl-D-isoglutamine benzyl ester)-α-D-mannopyranoside To a solution of benzyl 2-acetamido-4,6-O-benzylidene-3-O-(D-1-carboxyethyl)-2-deoxy-α-D-mannopyranoside (251 mg) in dry N,N-dimethylformamide (3 ml) at −15° is added N methylmorpholine (65 μl) and isobutyl chloroformate (73 μl). After stirring 10 minutes at −15°, a precooled solution of L-alanyl-D-isoglutamine benzyl ester hydrochloride (221 mg) in DMF (2 ml) is added followed by N-methylmorpholine (75 μl). The reaction mixture is stirred at −15° for 4 hours and then allowed to warm to 0°. An aqueous solution of potassium hydrogen carbonate (2.5M, 3 ml) is added dropwise. The mixture is stirred at 0° for 30 minutes and poured into distilled water (70 ml). The aqueous mixture is neutralized with 2.5N HCl and concentrated to dryness. The residue is taken up in DMF (10 ml), the insoluble material filtered off, the filtrate adsorbed onto silica gel (2 g) and applied to a column of silica gel and eluted with 29:1 chloroform methanol. The fractions containing the desired product are combined and concentrated to afford benzyl 2-acetamido-4,6-O-benzylidene-2-deoxy-3-O-(D-2-propionyl-L-alanyl-D-isoglutamine benzyl ester)-α-D-mannopyranoside as a white amorphous solid; yield 92 mg. (23%), [α]$_D$+29° (c 0.55, acetic acid).

Step C: Preparation of 2-Acetamido-2-deoxy-3-O-(D-2-propionyl-L-alanyl-D-isoglutamine)-D-mannose A solution of benzyl-2-acetamido-4,6-O-benzylidene-2-deoxy-3-O-(D-2-propionyl-L-alanyl-D-isoglutamine benzyl ester)-α-D-mannopyranoside (86 mg) in glacial acetic acid (6 ml) is hydrogenolyzed in the presence of palladium black at room temperature overnight. The reaction mixture is filtered through Celite, the filtrate evaporated, and traces of acetic acid removed by several coevaporations with toluene. The residue is taken up in a small volume of methanol and the product precipitated by the addition of diethyl ether. The solid is filtered, dissolved in a small volume of water, and lyophilized to afford 2-acetamido-2-deoxy-3-O-(D-2-propionyl-L-alanyl-D-isoglutamine)-D-mannose as a white amorphous solid; yield 40 mg. The 300 MHz nmr spectrum in D$_2$O is in accord with the desired structure.

EXAMPLE 3

Preparation of 2-acetamido-2-deoxy-3-O-(L-2-propionyl-L-alanyl-D-isoglutamine)-D-glucose

Step A: Preparation of Benzyl 2-acetamido-4,6-O-benzylidene-2-deoxy-3-O-(L-2-propionyl-L-alanyl-D-isoglutamine benzyl ester) α-D-glucopyranoside To a solution of benzyl 2-acetamido-4,6-O-benzylidene-3-O-(L-1-carboxyethyl)-2-deoxy-α-D-glucopyranoside [prepared by the process set forth in J. M. Petit, P. Sinay, E. Walker, D. A. Jeanloz, and R. W. Jeanloz, Carbohyd Res., 24, 415 (1972)] (498.7 mg) in dry N,N dimethylformamide (3 ml) and hexamethylphosphorictriamide (6 ml) at −15° is added N-methylmorpholine (120 μl) and isobutyl chloroformate (140 μl) After stirring 20 minutes at −15°, a precooled solution of L-alanyl-D-isoglutamine benzyl ester hydrochloride (431.5 mg) in DMF (3 ml) is added.

The reaction mixture is stirred at −15° for 4 hours and then at 0° for 1½ hours. An aqueous solution of potassium hydrogen carbonate (2.5 M, 5 ml) is added dropwise. The mixture is stirred at 0° for 30 minutes and poured into vigorously-stirred distilled water (90 ml). The precipitated white solid is filtered off and washed thoroughly with water and then twice with diethyl ether before being dried in vacuo over phosphorus pentoxide at room temperature overnight to afford benzyl 2-acetamido-4,6-O-benzylidene-2-deoxy-3-O-propionyl-L-alanyl-D-isoglutamine benzyl ester)-α-D-glucopyranoside as a white solid; yield 710 mg (88%). The 300 MHz nmr spectrum in DMSO-d$_6$ is in accord with the desired structure.

Step B: Preparation of 2-acetamido-2-deoxy-3-O-(L-2-propionyl-L-alanyl-D-isoglutamine)-D-glucose A solution of benzyl 2-acetamido-4,6-O-benzylidene-2-deoxy-3-O-(L-2-propionyl-L-alanyl-D-isoglutamine benzyl ester)-α-D-glucopyranoside (230 mg) in glacial acetic acid (10 ml) is hydrogenolyzed in the presence of palladium added in the form of PdO (0.20 g) at room temperature overnight. The reaction mixture is filtered through Celite, the filtrate evaporated, and traces of acetic acid removed by several coevaporations with toluene. The residue is taken up in a small volume of methanol and applied to a column of silica gel (20 g) and eluted with 70:40:5 chloroform methanol water. The fractions containing the desired product are combined and concentrated. The residue is taken up in a small volume of water, insoluble material is filtered off, and the filtrate is lyophilized to afford 2-acetamido-2-deoxy-3-O-(L-2-propionyl-L-alanyl-D-isoglutamine)-D-glucose as a white amorphous solid; yield 75 mg (50%); [α]$_D$−20° (C 0.40, water).

EXAMPLE 4

Preparation of 2-benzamido-2-deoxy-3-(L-2-propionyl-L alanyl-D-isoglutamine)-D-glucose

Step A: Preparation of benzyl 2-benzamido-4,6-O-benzylidene-3-O-(L-1-carboxyethyl)-2-deoxy-α-D-glucopyranoside To a stirred solution of benzyl 2-benzamido-4,6-O-benzylidene-2-deoxy-α-D-glucopyranoside [prepared by the process set forth in P. H. Gross and R. W. Jeanloz, J. Org. Chem., 32, 2759 (1967)] (1.16 g) in freshly distilled dioxane (70 ml) at 95° is added sodium hydride (0.57 g, 50% oil suspension). After one hour, the temperature is lowered to 65° and then a solution of D-2-chloropropionic acid (0.42 g) in a small volume of dry dioxane is added. After one hour, additional 50% sodium hydride (2.2 g) is added, and stirring at 65° is continued overnight. Water (35 ml) is carefully added to the cooled mixture to decompose excess sodium hydride. A dark-colored lower layer which develops is discarded, and the upper layer is filtered, partially concentrated, and diluted with water (20 ml). The aqueous mixture is extracted with chloroform and then the aqueous layer is acidified to pH 3 at 0° by addition of 2.5 N HCl and extracted with chloroform (3X). The combined chloroform extracts (of the acidified aqueous mixture) are dried (sodium sulfate) and evaporated to afford syrupy benzyl 2-benzamido-4,6-O-benzylidene-3-O-(L-1-carboxyethyl)-2-deoxy-α-D-glucopyranoside (835 mg). The 300 MHz nmr spectrum in chloroform-d is in accord with the desired structure.

Step B: Preparation of benzyl 2-benzamido-4,6-O-benzylidene-2-deoxy-3-O-(L-2-propionyl-L-alanyl-D-isoglutamine benzyl ester)-α-D-glucopyranoside To a solution of benzyl 2-benzamido 4,6-O-benzylidene-3-O-(L-1-carboxyethyl)-2-deoxy-α-D-glucopyranoside (564 mg) in dry N,N-dimethylformamide (5 ml) at −15° are added successively N-methylmorpholine (120 μl) and isobutyl chloroformate (140 μl). After stirring 3 minutes at −15°, a precooled solution of L-alanyl-D-isoglutamine benzyl ester hydrochloride (432 mg) in DMF (5 ml) is added. The reaction mixture is stirred at −15° for 4 hours and the temperature increased to 0°. An aqueous solution of potassium hydrogen carbonate (2.5 M, 5 ml) is added dropwise and the mixture is stirred at 0° for 30 minutes and then poured into vigorously stirred distilled water (90 ml). The precipitated white solid is filtered, washed thoroughly with water and then with diethyl ether before being dried in vacuo over phosphorous pentoxide at room temperature overnight to afford benzyl 2-benzamido-4,6-O-benzylidene-2-deoxy-3-O-(L-2-propionyl-L-alanyl-D-isoglutamine benzyl ester)-α-D-glucopyranoside as a white solid; yield 803 mg (88%). The 300 MHz nmr spectrum in DMSO-$d_6$ is in accord with the desired structure.

Step C: Preparation of 2-benzamido-2-deoxy-3-O-(L-2-propionyl-L-alanyl-D-isoglutamine)-D-glucose A solution of benzyl 2-benzamido 4,6-O-benzylidene-2-deoxy-3-O-(L-2-propionyl-L-alanyl-D-isoglutamine benzyl ester)-α-glucopyranoside (250 mg) in glacial acetic acid (15 ml) is hydrogenolyzed in the presence of palladium black added in the form of palladium oxide (200 mg) at room temperature for 24 hours. The reaction mixture is then filtered through Celite, the filtrate evaporated, and traces of acetic acid removed by several coevaporations with toluene. The residue is taken up in a small volume of methanol and the product precipitated by addition of diethyl ether. 2-Benzamido2-deoxy-3-O-(L-2-propionyl-L-alanyl-D-isoglutamine)-D-glucose is obtained as an amorphous solid; yield 140 mg. The 300 MHz nmr spectrum in $D_2O$ is in accord with the desired structure.

EXAMPLE 5

Preparation of 2-acetamido-2-deoxy-3-O-(D-2-propionyl-D-alanyl-D-isoglutamine)-D-galactose

Step A: Preparation of Benzyl 2-acetamido-4,6-O-benzylidene-2-deoxy-3-O-(D-2-propionyl-D-alanyl-D-isoglutamine benzyl ester)-α-D-galactopyranoside A solution of benzyl 2-acetamido-4,6-O-benzylidene-3-O-(D-1-carboxyethyl)-2-deoxy-α-D-galactopyranoside (prepared by the process set forth in P. Sinay and R. W. Jeanloz, *Carbohyd. Res.*, 10, 189 (1969)](432 mg) in dry N,N-dimethylformamide (4 ml) and hexamethylphosphorictriamide (1 ml) is cooled to −15° and treated with N methylmorpholine (110 μl) and isobutyl chloroformate (125 μl). After stirring 15 minutes at −15°, a precooled solution of D-alanyl-L-isoglutamine benzyl ester hydrochloride (341 mg) in 4 ml DMF is added followed by N-methylpholine (120 μl). The reaction mixture is allowed to stir at −15° for 3 hours and then allowed to warm to 0°. An aqueous solution of potassium hydrogen carbonate (2.5 M, 3 ml) is added dropwise. The mixture is stirred at 0° for 30 minutes, and poured into distilled water (100 ml). The aqueous mixture is stirred at room temperature overnight, and the resulting solid material is filtered off, washed thoroughly with water and then with diethyl ether. Drying in vacuo over phosphorus pentoxide overnight affords benzyl 2-acetamido-4,6-O-benzylidene-2-deoxy-3O-(D-2-propionyl-D-alanyl-D-isoglutamine benzyl ester)-α-D-galactopyranoside as a white solid; yield 615 mg (88%), m.p. 199°–209°, $[\alpha]_D = +107°$ (c 1.03 DMF).

Step B: Preparation of 2-acetamido-2-deoxy-3-O-(D-2-propionyl-D-alanyl-D-isoglutamine)-D-galactose A solution of benzyl 2-acetamido-4,6-O-benzylidene-2-deoxy-3-O-(D-2-propionyl-D-alanyl-D-isoglutamine benzyl ester)-α-D-galactopyranoside (400 mg) in glacial acetic acid (10 ml) is hydrogenolyzed at atmospheric pressure and room temperature in the presence of palladium (added as PdO) over the course of seven days (several additions and one change with fresh palladium oxide are made; total present at any one time is 0.10–0.25 g). The reaction mixture is filtered through Celite, the filtrate evaporated, and traces of acetic acid removed by several coevaporations with toluene. The residue is taken up into a small volume of methanol and applied to a column of silica gel (35 g) and eluted with 70:40:5 chloroform methanol water. The fractions containing the desired product are combined and concentrated. The residue is taken up in a small volume of methanol and precipitated by addition of diethyl ether. The solid is filtered, dissolved in water (2 ml) and lyophilized to afford 2-acetamido-2-deoxy-3-O-(D-2-propionyl-D-alanyl-D-isoglutamine)-D-galactose as a white amorphous solid; yield 75 mg (29%). The 300 MHz nmr spectrum in $D_2O$ is in accord with the desired structure.

EXAMPLE 6

Preparation of 2-acetamido-2-deoxy-3-O-(D-2-propionyl-L-seryl-D-isoglutamine)-D-galactose

Step A: Preparation of benzyl 2-acetamido-4,6-O-benzylidene-2-deoxy-3-O-(D-2-propionyl-L-(O-benzyl)seryl-D-isoglutamine benzyl ester)-α-D-galactopyranoside A solution of benzyl 2-acetamido-4,6-O-benzylidene-3-O-(D-1-carboxyethyl)-2-deoxy-α-D-galactopyranoside [prepared by the process set forth in P. Sinay and R. W. Jeanloz, *Carbohyd. Res.* 10, 189 (1969)] (500 mg) in dry N,N-dimethylformamide (4 ml) is cooled to −15° and 120 μl of N-methylmorpholine and 140 μl of isobutyl chloroformate is added. After stirring 20 minutes at −15°, a precooled solution of O-benzyl-L-seryl-D-isoglutamine benzyl ester hydrochloride (557 mg) in DMF (4 ml) with N methylmorpholine (140 μl) is added. The reaction mixture is stirred at −15° for 2½ hours and then allowed to warm to 0°. An aqueous solution of potassium hydrogen carbonate (2.5 M, 3 ml) is added dropwise. The mixture is stirred at 0° for 30 minutes and then poured into distilled water (80 ml). The precipitated material is filtered off and washed with several portions of water. The white material is ground to a powder and dried in vacuo over phosphorus pentoxide to afford benzyl 2-acetamido-4,6-O-benzylidene-2-deoxy-3-O-(D-2-propionyl-L-(O-benzyl)-seryl-D-isoglutamine benzyl ester)-α-D-galactopyranoside as a white solid; yield 800 mg (87%), m.p. 129°–131° (from DMF/95% EtOH), $[\alpha]_D$ +111° (c 1.0, DMF).

Step B: Preparation of 2-acetamido-2-deoxy-3-O-(D-2-propionyl-L-seryl-D-isoglutamine)-D-galactose A solution of benzyl 2-acetamido-4,6-O-benzylidene-2-deoxy-3-O-(D-2-propionyl-L-(O-benzyl)seryl-D-isoglutamine benzyl ester)-α-D-alactopyranoside (596.7 mg) in glacial acetic acid (10 ml) is hydrogenolyzed at room temperature in the presence of palladium [added as PdO, 0.30 g]. The reaction is incomplete after 20 hours; therefore, the catalyst is filtered off through Celite and to the filtrate is added 10% palladium on charcoal (0.5 g) and the hydrogenolysis is continued under 40 p.s.i. hydrogen. After 20 hours, the reaction is interrupted, the catalyst is filtered off through Celite, the filtrate is charged with fresh 10% palladium-on-charcoal (0.5 g) and the reaction is continued for another 20 hours under 40 p.s.i. hydrogen. The catalyst is filtered off through Celite, the filtrate evaporated, and traces of acetic acid removed by several coevaporations with toluene. The residue is taken up in a small volume of methanol and adsorbed onto silica gel (40 g) and eluted successively with 9:1 $CHCl_3/MeOH$ and 70:40:8 $CHCl_3/MeOH/H_2O$. The fractions containing the desired product are combined and concentrated. The residue is taken up in a small volume of water, filtered through sintered glass, and lyophilized to afford 2-acetamido-2-deoxy-3-O-(D-2-propionyl-L-seryl-D-isoglutamine)-D-galactose as a white amorphous solid; yield 106 mg (30%). The 300 MHz nmr spectrum in $D_2O$ is in accord with the desired structure.

EXAMPLE 7

2-Acetamido-2-deoxy-3-O-(D-2-propionyl-L-phenylalanyl-D-isoglutamine)-D-galactose In like manner, substituting a stoichiometric equivalent amount of L-phenylalanyl-D-isoglutamine benzyl ester hydrochloride in Example 6 for L-alanyl-D-isoglutamine benzyl ester hydro chloride, there are obtained the protected glycopeptide derivative, benzyl 2-acetamido-4,6-O-benzylidene-2-deoxy-3-O-(D-2-propionyl-L-phenylalanyl-D-isoglutamine benzyl ester)-α-D-galactopyranoside and subsequently the deprotected dipeptidyl saccharide, 2-acetamido-2-deoxy-3-O-(D-2-propionyl-L-phenylalanyl-D-isoglutamine)-D-galactose.

EXAMPLE 8

2-Acetamido-2-deoxy-3-O-(D-2-propionyl-L-prolyl-D-isoglutamine)-D-galactose

In like manner, substituting a stoichiometric equivalent amount of L-prolyl-D-isoglutamine benzyl ester hydrochloride in Example 6 for L-alanyl-D-isoglutamine benzyl ester hydrochloride, there are obtained the protected glycopeptide derivative, benzyl 2-acetamido-4,6-O-benzylidene-2-deoxy-3-O-(D-2-propionyl-L-prolyl-D-isoglutamine benzyl ester)-α-D-galactopyranoside and subsequently the deprotected dipeptidyl sacc- haride, 2-acetamido 2-deoxy-3-O-(D-2-propionyl-L-prolyl-D-isoglutamine)-D-galactose.

EXAMPLE 9

2-Acetamido-2-deoxy-3-O-(D-2-propionyl-L-tyrosyl-D-isoglutamine)-D-galactose

In like manner, substituting a stoichiometric equivalent amount of O-benzyl-L-tyrosyl-D-isoglutamine benzyl ester hydrochloride in Example 6 for L-alanyl-D-isoglutamine benzyl ester hydrochloride, there are obtained the protected glycopeptide derivative, benzyl 2-acetamido-4,6-O-benzylidene-2-deoxy-3-O-(D-2-propionyl-O-benzyl-L-tyrosyl-D-isoglutamine benzyl ester)-α-D-galactopyranoside and subsequently the deprotected dipeptidyl saccharide, 2-acetamido-2-deoxy-3-O-(D-2-propionyl-L-tyrosyl-D-isoglutamine)-D-galactose.

EXAMPLE 10

2-Acetamido-2-deoxy-3-O-(D-2-propionyl-L-cysteinyl-D-isoglutamine)-D-galactose

In like manner, substituting a stoichiometric equivalent amount of S-benzyl-L-cysteinyl-D-isoglutamine benzyl ester hydrochloride in Example 6 for L-alanyl-D-isoglutamine benzyl ester hydrochloride, there are obtained the protected glycopeptide derivative, benzyl 2-acetamido-4,6-O-benzylidene-2-deoxy-3-O-(D-2-propionyl-S-benzyl-L-cysteinyl-D-isoglutamine benzyl ester)-α-D-galactopyranoside and subsequently the deprotected dipeptidyl saccharide, 2-acetamido-2-deoxy-3-O-(D-2-propionyl-L-cysteinyl-D-isoglutamine)-D-galactose.

EXAMPLE 11

Preparation of 2-acetamido-2-deoxy-3-O-(L-2-propionyl-L-alanyl-D-isoglutamine)-D-galactose.

Step A: Preparation of benzyl 2-acetamido-4,6-O-benzylidene-2-deoxy-3-O-(L-2-propionyl-L-alanyl-D-isoglutamine benzyl ester)-α-D-galactopyranoside To a solution of benzyl 2-acetamido-4,6,-O-benzylidene-3-O-(L-1-carboxyethyl)-2-deoxy-α-D-galactopyranoside [prepared by the process set forth in P. Sinay and R. W. Jeanloz, Carbohyd. Res., 10, 189 (1969)] (605 mg) in dry N,N-dimethylformamide (6 ml) at −15° is added N methylmorpholine (145 μl) and isobutyl chloroformate (170 μl). After stirring 20 minutes at −15°, a precooled solution of L-alanyl-D-isoglutamine benzyl ester hydrochloride (515 mg) with N-methylmorpholine (170 μl) in DMF (6 ml) is added. The reaction mixture is stirred at −15° for 4 hours, after which it is allowed to warm to 0°. An aqueous solution of potassium hydrogen carbonate (2.5 M, 6 ml) is added dropwise. The mixture is stirred at 0° for 30 minutes and then poured into vigorously stirred water (100 ml). A gummy solid is deposited on the sides of that flask. The creamy supernatant is decanted off and the remaining gum crystallized by trituration with diethyl ether. The supernatant emulsion is extracted once with diethyl ether and three times with ethyl acetate. The combined ethyl acetate extracts are washed once with water and concentrated. The residue is taken up in DMF and combined with a DMF solution of the previously crystallized material. The solution is concentrated to a syrup which is taken up in a small volume of 25:1 chloroformmethanol and applied to a column of silica gel (75 g). Elution with 25:1 chloroform-methanol followed by combination and concentration of the appropriate fractions affords benzyl 2-acetamido-4,6-O-benzylidene-2-deoxy-3-O-(L-2-propionyl-L-alanyl-D-isoglutamine benzyl ester)-α-D-galactopyranoside as a white solid; yield 542 mg (56%). The 300 MHz nmr spectrum in DMSO-$d_6$ is in accord with the desired structure.

Step B: Preparation of 2-acetamido-2-deoxy-3-O-(L-2-propionyl-L-alanyl-D-isoglutamine)-D-galactose A solution of benzyl 2-acetamido-4,6-O-benzylidene-2-deoxy-3-O-(L-2-propionyl-L-alanyl-D-isoglutamine benzyl ester)-α-D-galactopyranoside (355 mg) in glacial acetic acid (10 ml) is hydrogenolyzed in the presence of palladium (added in the form of PdO, 0.20 g) at room temperature for 3 days. The reaction mixture is filtered through Celite, the filtrate is diluted to 15 ml with glacial acetic acid, 10% palladium-on charcoal (0.4 g) is added, and hydrogenolysis is continued with shaking under 40 p.s.i. hydrogen overnight. The mixture is filtered through Celite and the filtrate is evaporated, with several co evaporations with toluene, to remove traces of acetic acid. Minor impurities are removed by chromatography over silica gel and elution with 60:40:10 chloroform-methanol-water. The residue is taken up in a minimal volume of methanol and precipitated by addition of ethyl ether. The solid is filtered, dissolved in a small volume of water, and lyophilized to afford 2-acetamido-2-deoxy-3-O-(L-2-propionyl-L-alanyl-D-isoglutamine)-D-galactose as an amorphous white solid, yield 165 mg (72%). The 300 MHz nmr spectrum in $D_2O$ is in accord with the desired structure.

EXAMPLE 12

Preparation of 2-acetamido-2-deoxy-3-O-(D-2-propionyl-L-alanyl-D-isoglutamine)-D-allose

Step A: Preparation of benzyl 2-acetamido-4,6-O-benzylidene-3-O-(D-1-carboxyethyl)-2-deoxy-α-D-allopyranoside To a stirred solution of benzyl 2-acetamido-4,6-O-benzylidene-2-deoxy-α-D-allopyranoside [prepared by the process set forth in W. Meyer zu Reckendorf, Chem. Ber. 102, 4207 (1969)] (1.00 g) in dry dioxane (70 ml) at 95° is added sodium hydride (0.57 g, 50% oil suspension). After one hour, the temperature is lowered to 65° and then a solution of L-2-chloropropionic acid (0.41 g) in a small volume of dioxane is added. After one hour, additional 50% sodium hydride (2.3 g) is added, and stirring at 65° is continued overnight. Water (35 ml) is carefully added to the cooled reaction mixture. A dark colored lower layer which develops is discarded, and the upper layer is filtered, partially concentrated, and diluted with water (20 ml). The aqueous mixture is extracted with chloroform and then the aqueous layer is acidified to pH 3 at 0° by addition of 2.5N HCl and extracted with chloroform (3x). The combined chloroform extracts (of the acidified aqueous mixture) are dried over anhydrous sodium sulfate and concentrated to give a yellow gummy residue (720 mg) consisting of benzyl 2-acetamido-4,6-O-benzylidene-3-O-(D-1-carboxyethyl)-2-deoxy-α-D-allopyranoside of sufficient purity for subseguent reaction (Step B). An analytical sample is obtained by applying the product mixture (279 mg) to preparative thin layer chromatography silica gel plates (3 Analtech 1000 μm silica gel GF, 8×8") and developing with 9:1 chloroform methanol. Extraction of the silica gel band containing the desired product with 9:1 chloroform methanol, decolorization of the combined extracts with activated charcoal, and concentration affords a glass (131 mg). The 300 MHz nmr spectrum in methanol-$d_4$ is consistent with the desired structure.

Step B: Preparation of benzyl 2-acetamido-4,6-O-benzylidene-2-deoxy-3-O-(D-2-propionyl-L-alanyl-D-isoglutamine benzyl ester)-α-D-allopyranoside To a solution of benzyl 2-acetamide-4,6-O-benzylidene-3-O-(D-1-carboxyethyl-2-deoxy-α-D-alloranoside (459 mg) in dry N,N-dimethylformamide (4 ml) at −15° is added N-methylmorpholine (110 μl) and isobutyl chloroformate (130 μl). After stirring 15 minutes at −15°, a precooled solution of L-alanyl-D-isoglutamine benzyl ester hydrochloride (389 mg) in DMF (4 ml) is added, followed by N-methylmorpholine (130 μl). The reaction mixture is stirred at −b 15° for 3½ hours and then allowed to warm to 0°. An aqueous solution of potassium hydrogen carbonate (2.5 M, 3 ml) is added dropwise. The mixture is stirred at 0° for 30 minutes and poured into distilled water (100 ml). The aqueous mixture is neutralized with 2.5 N HCl and concentrated to dryness. The residue is taken up in DMF (10 ml), the insoluble material filtered off, and the filtrate concentrated to a syrup.

Purification is achieved by applying the material on a column of silica gel packed with 5:1 chloroform-diethyl ether and elution with 20:10:1 chloroform diethyl ether methanol. The fractions containing the desired product are combined and concentrated to afford solid benzyl 2-acetamido-4,6-O-benzylidene-2-deoxy-3-O-(D-2-propionyl-L-alanyl-D-isoglutamine benzyl ester)-α-D-allopyranoside; yield 246 mg (33%). The 300 MHz nmr spectrum in DMSO-$d_6$ is in accord with the desired structure.

Step C: Preparation of 2-acetamido-2-deoxy-3-O-(D-2-propionyl-L-alanyl-D-isoglutamine)-D-allose A solution of benzyl 2-acetamido-4,6-O-benzylidene-3-O-(D-2-propionyl-L-alanyl-D-isoglutamine benzyl ester)-α-D-allopyranoside (200 mg) in glacial acetic acid (10 ml) is hydrogenolyzed in the presence of palladium black at room temperature overnight. The reaction mixture is filtered through Celite, the filtrate evaporated, and traces of acetic acid removed by several coevaporations with water and subsequently toluene. The residue is taken up in methanol, filtered, and concentrated to a material that is dissolved in a small volume of water and lyophilized to afford 2-acetamido-2-deoxy-3-O-(D-2-propionyl-L-alanyl-D-isoglutamine)-D-allose as a white amorphous solid; yield 115 mg. The 300 MHz nmr spectrum in $D_2O$ is in accord with the desired structure.

EXAMPLE 13

Preparation of
2-acetamido-2-deoxy-3-O-(L-2-propionyl-L-seryl-L-isoglutamine)-D-galactose

Step A: Preparation of benzyl 2-acetamido-4,6-O-benzylidene-2-deoxy-3-O-(L-2-propionyl-L-(O-benzyl)seryl-D-isoglutamine benzyl ester)-α-D-galactopyranoside To a solution of benzyl 2-acetamido-4,6-O-benzylidene-3-O-(L-1-carboxyethyl)-2-deoxy-α-D-galactopyranoside [prepared by the process set forth in P. Sinay and R. W. Jeanloz, *Carbohyd. Res.*, 10, 189 (1969)] (700 mg) in dry N,N-dimethylformamide (7 ml) at −15° is added N-methylmorpholine (170 μl) and isobutyl chloroformate (200 μl). After stirring 20 minutes at −15°, a precooled solution of O-benzyl-L-seryl-D-isoglutamine benzyl ester hydrochloride (781 mg) in DMF (7 ml) and N-methylmorpholine (200 μl) is added. The reaction mixture is stirred at −15° for 4 hours, and allowed to warm to 0°. An aqueous solution of potassium hydrogen carbonate (2.5M, 7 ml) is added dropwise. The mixture is stirred at 0° for 30 minutes and poured into vigorously stirred distilled water (120 ml). The precipitated material is filtered off, washed thoroughly with water and diethyl ether before drying in vacuo over phosphorus pentoxide at room temperature overnight to afford benzyl 2-acetamido-4,6-O-benzylidene-2-deoxy-3-O-[L-2-propionyl-L-(O-benzyl)-seryl-D-isoglutamine ester]-α-D-galactopyranoside as a white solid; yield 1.15 g (85%), m.p. 187°–196°; the 300 MHz nmr in DMSO-$d_6$ is in accord with the desired structure.

Step B: Preparation of 2-acetamido-2-deoxy-3-O-(L-2-propionyl-L-seryl-D-isoglutamine)-D-galactose A solution of benzyl 2-acetamido 4,6-O-benzylidene-2-deoxy-3-O-[L-2-propionyl-L-(O-benzyl)-seryl-D-isoglutamine benzyl ester]-α-D-galactopyranoside (599 mg) in glacial acetic acid (10 ml) is hydrogenolyzed in the presence of palladium (added in the form of PdO, 0.30 g) at room temperature for five days. The reaction mixture is filtered through Celite, the filtrate diluted to 15 ml with glacial acetic acid, and the hydrogenolysis is continued by shaking with 10% palladium-on-charcoal (0.5 g) under 40 p.s.i. hydrogen overnight. The reaction mixture is filtered through Celite, the filtrate concentrated and traces of acetic acid are removed by several co evaporations with toluene. The residue is taken up in a small volume of methanol and applied to a column of silica gel (35 g). Elution with 9:1 chloroform-methanol, 80:20:2 chloroform-methanol water, and 60:40:10 chloroform-methanol-water, successively, followed by combination and concentration of the fractions containing the desired product affords a residue which is taken up in a small volume of methanol. Precipitation with addition of diethyl ether, filtration, dissolution of the solid in water, and lyophilization affords 2-acetamido-2-deoxy-3-O-(L-2-propionyl-L-seryl-D-isoglutamine)-D-galactose as a white amorphous solid; yield 115 mg (33%). The 300 MHz nmr spectrum in $D_2O$ is in accord with the desired structure.

EXAMPLE 14

Preparation of 2-acetamido-2-deoxy 3-O-(L-2-propionyl-L-seryl-D-isoglutamine)-D-glucose

Step A: Preparation of benzyl 2-acetamido-4,6-O-benzylidene-2-deoxy-3-O-(L-2-propionyl-L-alanyl-D-isoglutamine benzyl ester)-α-glucopyranoside To a solution of benzyl 2-acetamido-4,6-O-benzylidene-3-O-(L-1-carboxyethyl)-2-deoxy-α-D-glucopyranoside [prepared by the process set forth in J. M. Petit, P. Sinay, E. Walker, D. A. Jeanloz, and R. W. Jeanloz, *Carbohyd. Res.*, 24, 415 (1972)] (699.5 mg) in dry N,N-dimethylformamide (10 ml) and hexamethylphosphorictriamide (5 ml) at −15° is added N-methylmorpholine (170 μl) and isobutyl chloroformate (200 μl). After stirring 20 minutes at −15°, a precooled solution of L-alanyl-D-isoglutamine benzyl ester hydrochloride (776.8 mg) and N-methylmorpholine (195 μl) in 7 ml DMF is added. The reaction mixture is stirred at −15° for 4 hours and stored at −17° overnight. The temperature is then allowed to rise to 0° and an aqueous solution of potassium hydrogen carbonate (2.5 M, 7 ml) is added dropwise with stirring. The mixture is stirred at 0° for 30 minutes and then poured into 150 ml stirred distilled water. The precipitated material is filtered off and washed thoroughly with water and then with diethyl ether before drying in vacuo over phosphorus pentoxide overnight to afford benzyl 2-acetamido-4,6-O-benzylidene-2-deoxy-3-O-(L-2-propionyl-L-alanyl-D-isoglutamine benzyl ester)-α-D-glucopyranoside as a white solid. The 300 MHz spectrum in DMSO-$d_6$ is in accord with the desired structure.

Step B: Preparation of 2-acetamido-2-deoxy-3-O-(L-2-propionyl-L-seryl-D-isoglutamine)-D-glucose A solution of benzyl 2-acetamido-4,6-O-benzylidene-2-deoxy-3-O-(L-2-propionyl-L-alanyl-D-isoglutamine benzyl ester)-α-D-glucopyraoside (623 mg) in glacial acetic acid (10 ml) is hydrogenolyzed at room temperature in the presence of palladium (added in the form of palladium oxide, 0.30 g) for 3 days. The reaction mixture is then filtered through Celite, the filtrate diluted to 25 ml with glacial acetic acid, 10% palladium-on-charcoal (0.5 g) is added, and the mixture is shaken under 40 p.s.i. hydrogen overnight. The reaction mixture is again filtered through Celite, evaporated, and coevaporated with toluene several times in order to remove traces of acetic acid. The residue is taken up in a small volume of methanol, applied to a column of silica gel (50 g), and eluted with 80:20:2 chloroform methanol-water followed by 60:40:10 chloroform methanol-water. Fractions containing the desired product are combined and concentrated. The residue is taken up in a small volume of methanol, precipitated by addition of diethyl ether, filtered, taken up in a small volume of water, and lyophilized to afford 2-acetamido-2-deoxy-3-O-(L-2-propionyl-L-seryl-D-isoglutamine)-D-glucose as a white amorphous solid; yield 119 mg (32.6%). The 300 MHz nmr spectrum in $D_2O$ is in accord with the desired structure.

EXAMPLE 15

2-Acetamido-2-deoxy-3-O-(L-2-propionyl-L-α-aminobutyryl-D-isoglutamine)-D-glucose In like manner, substituting a stoichiometric equivalent amount of L-α-aminobutyryl-D-isoglutamine benzyl ester hydrochloride in Example 14 for L-alanyl-D-isoglutamine benzyl ester hydrochloride, there are obtained the protected glycopeptide derivative, benzyl 2-acetamido-2-deoxy-3-O-(L-2-propionyl-L-α-aminobutyryl-D-isoglutamine benzyl ester)-α-D-glucopyranoside and subsequently the deprotected dipeptidyl saccharide, 2-acetamido-2-deoxy-3-O-(L-2-propionyl-L-α-aminobutyryl-D-isoglutamine)-D-glucose.

EXAMPLE 16

2-Acetamido-2-deoxy-3-O-(L-2-propionyl-L-norvalyl-D-isoglutamine)-D-glucose

In like manner, substituting a stoichiometric equivalent amount of L-norvalyl-D-isoglutamine benzyl ester hydrochloride in Example 14 for L-alanyl-D-isoglutamine benzyl ester hydrochloride, there are obtained the protected glycopeptide derivative, benzyl 2-acetamido-2-deoxy-3-O-(L-2-propionyl-L-norvalyl-D-isoglutamine benzyl ester)-α-D-glucopyranoside and subsequently the deprotected dipeptidyl saccharide, 2-acetamido-2-deoxy-3-O-(L-2-propionyl-L-norvalyl-D-isoglutamine)-D-glucose.

EXAMPLE 17

2 Acetamido 2 deoxy-3-0 (L-2-propionyl-D-norleucyl-D-isoglutamine)-D-glucose In like manner, substituting a stoichiometric equivalent amount of L-norleucyl-D-isoglutamine benzyl ester hydrochloride in Example 14 for L-alanyl-D-isoglutamine benzyl ester hydrochloride there are obtained the protected glycopeptide derivative, benzyl 2-acetamido-2-deoxy-3-O-(L-2-propionyl-L-norleucyl-D-isoglutamine benzyl ester)-α-D-glucopyranoside and subsequently the deprotected dipeptidyl saccharide, 2-acetamido-2-deoxy-3-O-(L-2-propionyl-L-norleucyl-D-isoglutamine)-D-glucose.

EXAMPLE 18

2-Acetamido-2-deoxy-3-O-(L-2-propionyl-L-alanyl-D-glutamic acid)-D-glucose

In like manner, substituting a stoichiometric equivalent amount of L-alanyl-D-glutamic acid dibenzyl ester hydrochloride in Example 14 for L-alanyl-D-isoglutamine benzyl ester hydrochloride, there are obtained the protected glycopeptide derivative, benzyl 2-acetamido-2-deoxy-3-O-(L-2-propionyl-D-alanyl-D-glutamic acid dibenzyl ester)-α-D-glucopyranoside and subsequently the deprotected dipeptidyl saccharide, 2-acetamido-2-deoxy-3-O-(L-2-propionyl-L-alanyl-D-glutamic acid)-D-glucose.

EXAMPLE 19

2-Acetamido-2-deoxy-3-O-(L-2-propionyl-L-alanyl-D-glutamic acid dimethyl ester)-D-glucose In like manner, substituting a stoichiometric equivalent amount of L-alanyl-D-glutamic acid dimethyl ester hydrochloride in Example 14 for L-alanyl-D-isoglutamine benzyl ester hydrochloride, there are obtained the protected glycopeptide derivative, benzyl 2-acetamido-2-deoxy-3-O-L-2-propionyl-L-alanyl-D-glutamic acid dimethyl ester)-α-D-glucopyranoside and subsequently the deprotected dipeptidyl saccharide, 2-acetamido-2-deoxy-3-O-(L-2-propionyl-L-alanyl-D-glutamic acid dimethyl ester)-D-glucose.

EXAMPLE 20

2-Acetamido-2-deoxy-3-O-(L-2-propionyl-L-alanyl-D-glutamic acid methylamide)-D-glucose In like manner, substituting a stoichiometric equivalent amount of L-alanyl-D-glutamic acid methylamide hydrochloride in Example 14 for L-alanyl-D-isoglutamine benzyl ester hydro chloride, there are obtained the protected glycopeptide derivative, benzyl 2-acetamido 2-deoxy-3-O-(L-2-propionyl-L-alanyl-D-glutamic acid methylamide)-α-D-glucopyranoside, and subsequently the deprotected dipeptidyl saccharide, 2-acetamido-2-deoxy-3-O-(L-2-propionyl-L-alanyl-D-glutamic acid methylamide)-D-glucose.

EXAMPLE 21

Preparation of 2-acetamido-2-deoxy-3-O-(D-2-propionyl-L-alanyl-D-isoglutamine)-6-O-stearoyl-D-allose

Step A: Preparation of benzyl 2-acetamido-2-deoxy-3-O-(D-2-propionyl-L-alanyl-D-isoglutamine benzyl ester)-α-D-allopyranoside Benzyl-2-acetamido-4,6-O-benzylidene-2-deoxy-3-O-(D-2-propionyl-L-alanyl-D-isoglutamine benzyl ester)-α-D-allopyranoside (305 mg) is stirred in 60% aqueous acetic acid (12 ml) at 90° for 20 minutes. The cooled solution is concentrated and traces of acetic acid are removed by two coevaporations with water followed by two coevaporations with toluene. The residue is triturated with diethyl ether, and the resulting solid is filtered, washed thoroughly with diethyl ether and dried in vacuo to afford benzyl 2-acetamido-2-deoxy-3-O-(D-2-propionyl-L-alanyl-D-isoglutamine benzyl ester)α-D-allopyranoside as a white amorphous solid; yield 204 mg (76%). The 300 MHz nmr spectrum in DMSO-$d_6$ is in accord with the desired structure.

Step B: Preparation of benzyl 2-acetamido-2-deoxy-3-O-(D-2-propionyl-L-alanyl-D-isoglutamine benzyl ester)-6-O-stearoyl-α-D-allopyranoside To a solution of benzyl 2-acetamido-2-deoxy 3-O-(D-2-propionyl-L-alanyl-D-isoglutamine benzyl ester)-α-D-allopyranoside (185 mg) in pyridine (9 ml) was added stearoyl chloride (110 μl). After stirring at room temperature for 1 hour, additional stearoyl chloride (20 μl) is added and the solution is stirred at room temperature overnight. Methanol (0.5 ml) is added and stirring is continued for 15 minutes before evaporation to dryness. The residue is dissolved in chloroform (20 ml) and the solution is washed with water (20 ml), dried over anhydrous sodium sulfate, and concentrated to afford a residue which solidifies upon trituration with petroleum ether. The solid is filtered, washed with petroleum ether, and dried in vacuo. The material (162 mg) is taken up in a small volume of chloroform, applied to a column of silica gel (18 5 g), and eluted with 30:1 chloroform methanol. Fractions containing the desired product are combined and concentrated. The residue is triturated with diethyl ether-petroleum ether to afford benzyl 2-acetamido-2-deoxy-3-O-(D-2-propionyl-L-alanyl D-isoglutamine benzyl ester)-6-O-stearoyl-α-D-allopyranoside as a white amorphous solid, yield 98 mg (38%), [α]$_D$ +15° (c 0.97, chloroform), The 300 MHz nmr spectrum in DMSO-d$_6$ is in accord with the desired structure.

Step C: Preparation of 2-acetamido-2-deoxy-3-O-(D-2-propionyl-L-alanyl-D-isoglutamine)-6-O-stearoyl-D-allose A solution of benzyl 2-acetamido-2-deoxy-3-O-(D-2-propionyl-L-alanyl-D-isoglutamine benzyl ester)-6-O-stearoyl-α-D-allopyranoside (79 mg) in glacial acetic acid (10 ml) is hydrogenolyzed overnight in the presence of 10% palladium-on-charcoal (0.3 g). The reaction mixture is filtered through Celite, the filtrate evaporated, and traces of acetic acid removed by several coevaporations with toluene. The residue is taken up in a minimal volume of methanol, applied to a column of silica gel, and eluted successively with 9:1 chloroform methanol, 80:20:2 chloroform methanol water, and 70:40:5 chloroform methanol-water. Fractions containing the desired product are combined and concentrated, and the residue is taken up in a small volume of water and lyophilized to afford 2-acetamido-2-deoxy-3-O-(D-2-propionyl-L-alanyl-D-isoglutamine)-6-O-stearoyl-D-allose as a white amorphous solid, yield 42 mg (65%). The 300 MHz nmr spectra in D$_2$O and DMSO-d$_6$ are in accord with the desired structure.

EXAMPLE 22

Preparation of 2-acetamido-2-deoxy-3-O-(L-2-propionyl-L-alanyl-D-isoglutamine)-6-O-stearoyl-D-glucose

Step A: Preparation of benzyl 2-acetamido-2-deoxy-3-O-(L-2-propionyl L-alanyl-D-isoglutamine benzyl ester-α-D-glucopyranoside Benzyl 2-acetamido-4,6-O-benzylidene-2-deoxy-3-O-(L-2-propionyl-L-alanyl-D-isoglutamine benzyl ester)-α-D-glucopyranoside (124 mg) is stirred in 60% aqueous acetic acid (5 ml) at 90° for 20 minutes. The cooled solution is concentrated and traces of acetic acid are removed by two coevaporations with water followed by two coevaporations with toluene. The residue is triturated with diethyl ether and the resulting solid is filtered, washed thoroughly with diethyl ether, and dried in vacuo to afford benzyl 2-acetamido-2-deoxy-3-O-(L-2-propionyl-L-alanyl-D-isoglutamine benzyl ester)-α-D-glucopyranoside as a white amorphous solid; yield 98 mg (89%) The 300 MHz nmr spectrum in DMSOd$_6$ is in accord with the desired structure.

Step B: Preparation of benzyl 2-acetamido-2-deoxy-3-O-(L-2-propionyl-L-alanyl-D-isoglutamine benzyl ester)-6-O-stearoyl-α-D-glucopyranoside To a solution of benzyl 2-acetamido-2-deoxy-3-O-(L-2-propionyl-L-alanyl-D-isoglutamine benzyl ester)-α-D-glucopyranoside (94 mg) in pyridine (5 ml) is added stearoyl chloride (56 μl). After stirring at room temperature for 1 hour, additional stearoyl chloride (10 μl) is added and the solution is stirred at room temperature overnight. Methanol (0.5 ml) is added and stirring is continued for 15 minutes before concentrating to dryness. The residue is dissolved in chloroform (20 ml) and the solution is washed with saturated aqueous sodium hydrogen carbonate (20 ml) followed by water (20 ml), dried over anhydrous sodium sulfate, and concentrated to afford a residue which is taken up in a minimal volume of chloroform and applied to a column of silica gel (9.9 g). Elution with 30:1 chloroformmethanol and combination and concentration of the fractions containing the desired product affords benzyl 2-acetamido-2-deoxy-3-O-(L-2-propionyl-L-alanyl-D-isoglutamine benzyl ester)-6-O-stearoyl-α-D-glucopyranoside as an amorphous solid; yield 47 mg (36%). Crystallization is achieved from ethyl acetate ether petroleum ether; m.p. 145°-150°, [α]$_D$+19° (c, 1.04, CHCl$_3$). The 300 MHz nmr spectrum in DMSO-d$_6$ is in accord with the desired structure.

Step C: Preparation of 2-acetamido-2-deoxy-3-O-(L-2-propionyl-L-alanyl-D-isoglutamine)-6-O-stearoyl-D-glucose A solution of benzyl 2-acetamido-2-deoxy-3-O-(L-2-propionyl-L-alanyl-D-isoglutamine benzyl ester)-6-O-stearoyl-α-D-glucopyranoside (40 mg) in glacial acetic acid (5 ml) is hydrogenolyzed in the presence of 10% palladium on charcoal (0.2 g) for 60 hours. The reaction mixture is filtered through Celite, the filtrate evaporated, and traces of acetic acid removed by several coevaporations with toluene. The residue is taken up in a minimal volume of methanol, applied to a column of silica gel (6 g), and eluted with 9:1 chloroform methanol (20 ml) followed by 80:20:2 chloroform methanol water. Fractions containing the desired product are combined and concentrated and the residue is taken up in a small volume of water and lyophilized to afford 2-acetamido-2-deoxy-3-O-(L-2-propionyl-D-alanyl-L-isoglutamine)-6-O-stearoyl-D-glucose as a white amorphous solid; yield 13 mg (40%). The 300 MHz nmr spectra in DMSO-d$_6$ and D$_2$O are in accord with the desired structure.

EXAMPLE 23

Preparation of ethyl 2-acetamido-2-deoxy-3-O-(D-2-propionyl-L-alanyl-D-isoglutamine)-α-D-mannopyranoside

Step A: Preparation of ethyl 2-acetamido-4,6-O-benzylidene-3-O-(D-1-carboxyethyl)-2-deoxy-α-D-mannopyranoside To a stirred solution of ethyl 2-acetamido-4,6-O-benzylidene-2-deoxy-α-D-mannopyranoside (0.95 g) in dry dioxane (80 ml) at 90° is added sodium hydride (0.67 g, 50% oil suspension). After 1 hour the temperature is lowered to 65° and then a solution of p-2-chloropropionic acid (0.46 g) in a small volume of dioxane is added. After one hour additional 50% sodium hydride (2.65 g) is added and stirring at 65° is continued overnight. Water (50 ml) is carefully added to the cooled reaction mixture. The resulting solution is concentrated to a small volume and diluted with water (60 ml). The aqueous mixture is extracted twice with chloroform and filtered through Celite, and then the aqueous layer is acidified to pH 3 at 0° by addition of 2.5N HCl and extracted with chloroform (3 x). The combined chloroform extracts of the acidified aqueous mixture are washed with water, dried over anhydrous magnesium sulfate, and concentrated to afford ethyl 2-acetamido-4,6-O-benzylidene-3-O-(D-1-carboxyethyl)-2-deoxy-α-D-mannopyranoside as a syrup; yield 731 mg (63%). Crystallization is achieved from ethyl acetate-petroleum ether. The 300 MHz nmr spectrum in methanol-d₄ is in accord with the desired structure, mp 173°–173.5°, [α]_D+22° (c, 1.06, methanol).

Step B: Preparation of ethyl 2-acetamido-4,6-O-benzylidene-2-deoxy-3-O-(D-2-propionyl-L-alanyl-D-isoglutamine benzyl ester)-α-D-mannopyranoside To a solution of ethyl 2-acetamido-4,6-O-benzylidene-3-O-(D-1-carboxyethyl)-2-deoxy-α-D-mannopyranoside (557 mg) in dry N,N-dimethylformamide (5 ml) at −15° is added N-methylmorpholine (155 μl) and isobutyl chloroformate (180 μl). After stirring 10 minutes at −15°, a precooled solution of L-alanyl-D-isoglutamine benzyl ester hydrochloride (470 mg) in DMF (3 ml) is added followed by N-methyl morpholine (155 μl). The reaction mixture is stirred at −15° for 4 hours and then allowed to warm to 0°. An aqueous solution of potassium hydrogen carbonate (2.5 M, 3 ml) is added dropwise. The mixture is stirred at 0° for 30 minutes and poured into distilled water (80 ml). The aqueous mixture is concentrated to dryness. The residue is taken up in DMF and adsorbed onto silica gel (2.5 g). The mixture is applied to a column of silica gel (50 g) and eluted with 29:1 chloroform methanol. The fractions containing the desired product are combined and concentrated. Trituration of the residue with diethyl ether affords ethyl 2-acetamido 4,6 0-O-benzylidene-2-deoxy-3-O-(D-2-propionyl-L-alanyl-D-isoglutamine benzyl ester)-α-D-mannopyranoside as a white crystalline solid; yield 615 mg (65%), mp 162°–164°, [α]_D+13° (c, 1.0, DMF). The 300 MHz nmr spectrum in DMSO-d₆ is in accord with the desired structure.

Step C: Preparation of ethyl 2-acetamido-2-deoxy-3-O-(D-2-propionyl-L-alanyl-D-isoglutamine)-α-D-mannopyranoside A solution of ethyl 2-acetamido-4,6-O-benzylidene-2-deoxy-3-O-(D-2-propionyl-L-alanyl-D-isoglutamine benzyl ester)-α-D-mannopyranoside (402 mg) in glacial acetic acid (15 ml) is hydrogenolyzed in the presence of palladium black (0.15 g) at room temperature overnight. The reaction mixture is filtered through Celite, the filtrate evaporated, and traces of acetic acid removed by several co evaporations with water and toluene. The residue is dissolved in a small volume of water and lyophilized to afford ethyl 2-acetamido-2-deoxy-3-O-(D-2-propionyl-L-alanyl-D-isoglutamine)-α-D-mannopyranoside as a white amorphous solid; yield 273 mg (91%), [α]_D+28° (c, 0.50, H₂O). The 300 MHz nmr spectrum in D₂O is in accord with the desired structure.

EXAMPLE 24

Preparation of 2-acetamido-4,6-di-O-acetyl-2-deoxy-3-O-(D-2-propionyl-L-alanyl-D-isoglutamine)-D-allose

Step A: Preparation of benzyl 2-acetamido-4,6-di-O-acetyl-2-deoxy-3-O-(D-2-propionyl-L-alanyl-D-isoglutamine benzyl ester)-α-D-allopyranoside To a solution of benzyl 2-acetamido-2-deoxy-3-O-(D-2-propionyl-L-alanyl-D-isoglutamine benzyl ester)-α-D-allopyranoside (153 mg) in N,N-dimethylformamide (3 ml) is added pyridine (2 ml) and acetic anhydride (1 ml). The solution is stirred at room temperature for 5 hours, after which additional acetic anhydride (0.5 ml) is added and stirring at room temperature was continued overnight. The solution is then evaporated and coevaporated several times with toluene. After drying the residue under high vacuum, the residue is taken up in a small volume of ethyl acetate, the solution applied to a column of silica gel (20 g), and eluted with 12:1 chloroform-methanol. Combination and evaporation of the appropriate fractions afford benzyl 2-acetamido-4,6-di-O-acetyl-2-deoxy-3-O-(D-2-propionyl-L-alanyl-D-isoglutamine benzyl ester)-α-D-allopyranoside as a white amorphous solid; yield 139 mg (81%). The 300 MHz nmr spectrum in DMSO-d₆ is in accord with the desired structure.

Step B: Preparation of 2-acetamido-4,6-di-O-acetyl-2-deoxy-3-O-(D-2-propionyl-L-alanyl-D-isoglutamine)-D-allose A solution of benzyl 2-acetamido-4,6-di-O-acetyl-2-deoxy-O-(D-2-propionyl-L-alanyl-D-isoglutamine benzyl ester)-α-D-allopyranoside (125 mg) in glacial acetic acid (6 ml) is hydrogenolyzed at room temperature in the presence of palladium (added in the form of palladium oxide, 0.12 g) for 65 hours. The reaction mixture is filtered through Celite. The filtrate is concentrated and traces of acetic acid are removed by several coevaporations with toluene. The residue is taken up in methanol, a small amount of insoluble material is removed by filtration through sintered glass, and the product is precipitated by addition of diethyl ether. The solid is filtered, dissolved in a small volume of water, and lyophilized to afford 2-acetamido-4,6-di-O-acetyl-2-deoxy-3-O-(D-2-propionyl-L-alanyl-D-isoglutamine)-D-allose as a white amorphous solid; yield 54 mg (57%). The 300 MHz nmr spectrum in D₂O is in accord with the desired structure.

EXAMPLE 25

Preparation of benzyl 2-acetamido-4,6-di-O-acetyl-2-deoxy-3-O-(D-2-propionyl-L-alanyl-D-isoglutamine)-α-D-allopyranoside A mixture of benzyl 2-acetamido-4,6-di-O-acetyl-2-deoxy-3-O-(D-2-propionyl-L-alanyl-D-isoglutamine benzyl ester)-α-D-allopyranoside (50 mg) in ethanol (5 ml) containing acetic acid (0.5 ml) is hydrogenolyzed at room temperature in the presence of 10% palladium on-charcoal (50 mg) for 24 hours. The reaction mixture is filtered through Celite, the filtrate evaporated, and traces of acetic acid removed by several coevaporations with toluene. The residue is taken up in the minimal volume of methanol, applied to a column of silica gel, and the column developed with 9:1 chloroform methanol followed by 80:20:2 chloroform methanol water. Fractions containing the desired product are combined, evaporated, and the residue is taken up in a small volume of water and lyophilized to afford benzyl 2-acetamido-4,6-di-O-acetyl-2-deoxy-3-O-(D-2-propionyl-L-alanyl-D-isoglutamine)-α-D-allopyranoside; yield 28 mg (64%). The 300 MHz nmr spectrum in DMSO-d₆ is in accord with the desired structure.

EXAMPLE 26

Preparation of p-aminophenyl 2-acetamido-2-deoxy-3-O-(L-2-propionyl-L-alanyl-L-isoglutamine)-β-D-glucopyranoside

Step A: Preparation of p-nitrophenyl-2-acetamido-4,6-O-benzylidene-3-O-(L-1-carboxyethyl)-2-deoxy-β-D-glucopyranoside To a solution of p-nitrophenyl-2-acetamido-4,6-O-benzylidene-2-deoxy-β-D-glucopyranoside [prepared by the process set forth in R. W. Jeanloz, E. Walker, and P. Sinay, *Carbohydr. Res.*, 6, 184 (1968)] (1.2 g) in dry dioxane (250 ml) is added at 95° sodium hydride (400 mg, 50% oil dispersion). After one hour, the temperature is lowered to 65° and then a solution of 2-chloropropionic acid (1.1 g) in a small volume of dry dioxane is added. After one hour, additional 50% sodium hydride (1 g) is added, and stirring at 65° is continued overnight. Water (70 ml) is added to the cooled mixture to decompose excess sodium hydride. A dark-colored lower layer which develops is discarded, and the upper layer is filtered, partially concentrated, and diluted with water (150 ml). The aqueous mixture is extracted with chloroform, and the aqueous layer is filtered and acidified to pH 3 at 0° by addition of 2.5 N HCl. The resulting precipitate is extracted with chloroform, the combined organic extracts dried (magnesium sulfate), and evaporated to a residue that is dissolved in warm methanol (40 ml) and the product precipitated by addition of water. The solid is filtered and dried in vacuo over phosphorus pentoxide to afford p-nitrophenyl 2-acetamido-4,6-O-benzylidene-3-O-(L-1-carboxyethyl)-2-deoxy-$\beta$-D-glucopyranoside as a white powder; yield 383 mg. The 300 MHz nmr spectrum in chloroform d is in accord with the desired structure.

Step B: Preparation of p-nitrophenyl-2-acetamido-4,6-O-benzylidene-2-deoxy-3-O-(L-2-propionyl-L-alanyl-D-isoglutamine benzyl ester-$\beta$-D-glucopyranoside To a solution of p-nitrophenyl-2-acetamido-4,6-O-benzylidene-3-O-(L-1-carboxyethyl)-2-deoxy-$\beta$-D-glucopyranoside (357 mg) in dry N,N-dimethylformamide (4 ml) at $-15°$ are added successively N-methylmorpholine (79 $\mu$l) and isobutyl chloroformate (93 $\mu$l). After stirring 3 minutes at $-15°$ a precooled solution of L-alanyl-D-isoglutamine benzyl ester hydrochloride (285 mg) in dry DMF (2 ml) is added The reaction mixture is stirred at $-15°$ for 2 hours and the temperature increase to 0°. An aqueous solution of potassium hydrogen carbonate (2.5 M, 3 ml) is added dropwise and the mixture is stirred at 0° for 30 minutes and then poured into distilled water (100 ml). The precipitated solid is filtered, the solid washed thoroughly with water and then diethyl ether. After drying in vacuo over phosphorous pentoxide, p-nitrophenyl 2-acetamido-4,6-O-benzylidene-2-deoxy-3-O-(L-2-propionyl-L-alanyl-D-isoglutamine benzyl ester)-$\beta$-D-glucopyranoside is obtained as a white solid; yield 523 mg (93%). The 300 MHz nmr spectrum in DMSO-d$_6$ is in accord with the desired structure.

Step C: Preparation of p-nitrophenyl-2-acetamido-2-deoxy-3-O-(L-2-propionyl-L-alanyl-D-isoglutamine benzyl ester)-$\beta$-D-glucopyranoside A mixture of p-nitrophenyl 2-acetamido-4,6-O-benzylidene-2-deoxy-3-O-(L-2-propionyl-L-alanyl-D-isoglutamine benzyl ester)-$\beta$-D-glucopyranoside (514 mg) in 60% aqueous acetic acid (40 ml) is stirred at 90° for 30 minutes. The resulting solution is then evaporated and coevaporated several times with toluene to remove traces of acetic acid. After drying in vacuo over phosphorous pentoxide, p-nitrophenyl 2-acetamido-2-deoxy-3-O-(L-2-propionyl-L-alanyl-D-isoglutamine benzyl ester)-$\beta$-D-glucopyranoside is obtained as a white solid; yield 328 mg (72%). The 300 MHz nmr spectrum in methanol-d$_4$ is in accord with the desired structure.

Step D: Preparation of p-aminophenyl-2-acetamido-2-deoxy-3-O-(L-2-propionyl-L-alanyl-D-isoglutamine)-$\beta$-D-glucopyranoside A solution of p nitrophenyl 2-acetamido-2-deoxy-3-O-(L-2-propionyl-L-alanyl-D-isoglutamine benzyl ester)-$\beta$-D-glucopyranoside (310 mg) in glacial acetic acid (10 ml) is hydrogenolyzed in the presence of 5% palladium-on-charcoal (300 mg) at room temperature overnight. The catalyst is removed by filtration through Celite, the filtrate is evaporated and coevaporated several times with toluene. The residue is dissolved in the minimal volume of methanol, and the solution is applied to a column of silica gel (30 g). Development is effected with at first 9:1 chloroform-methanol, then 80:20:2 chloroform methanol-water, and finally with 60:40:10 chloroform-methanol water. The fractions containing pure product are combined and evaporated to a residue that is taken up in a little methanol and the product precipitated by addition of diethyl ether. The solid is filtered and dried in vacuo over phosphorus pentoxide to afford p-aminophenyl-2-acetamido-2-deoxy-3-O-(L-2-propionyl-L-alanyl-D-isoglutamine)$\beta$-D-glucopyranoside as a white solid; yield 169 mg (66%). The 300 MHz nmr spectrum in D$_2$O is in accord with the desired structure.

It is reasonably believed on the basis of the data that the disclosed invention pharmaceutical compositions herein, containing the disclosed dipeptidyl saccharides, either alone, or in combination with an anti AIDS drug, will provide a human host, who is immunocompromised as a result of infection or contact with an AIDS related virus, with enhanced host resistance to "opportunistic" bacterial, fungal, or viral infection, including Kaposi's sarcoma and Pneumocystis pneumonia.

What is claimed is:

1. A composition for enhancing host resistance against opportunisic bacterial, fungal or viral infection in a human host immunocompromised by an AIDS-related virus comprising a compound:

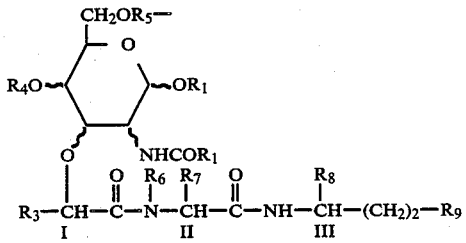

provided said glycose is not 2-amino-2-deoxy-D-glucose, wherein

R$_1$ is hydrogen; alkyl of 1 to 7 carbon atoms optionally substituted by hydroxy, mercapto, alkoxy of 1 to 3 carbon atoms, alkyl mercapto of 1 to 3 carbon atoms, hydroxy or mercapto esterified by an acid of 1 to 4 carbon atoms, halogen, carboxy; phenyl, benzyl each optionally substituted by alkyl of 1 to 3 carbon atoms, lower alkyldioxy, amino, trifluoromethyl, hydroxy, mercapto, hydroxy or mercapto etherified by alkyl of 1 to 3 carbon atoms, or hydroxy or mercapto esterified by an acid of 1 to 4 carbon atoms;

R$_2$ is alkyl of 1 to 7 carbon atoms optionally substituted by hydroxy, mercapto, alkoxy of 1 to 3 carbon atoms, alkyl mercapto of 1 to 3 carbon atoms, hydroxy or mercapto esterified by an acid of 1 to 4 carbon atoms, halogen, carboxyl, carboxyl esterified by an alcohol of 1 to 3 carbon atoms, or amidated carboxyl; phenyl, optionally substituted by alkyl of 1 to 3 carbon atoms, lower alkyldioxy, amino, trifluoromethyl, hydroxy, mercapto, hydroxy or mercapto etherified by alkyl of 1 to 3 carbon atoms, or hydroxy or mercapto esterified by an acid of 1 to 4 carbon atoms;

$R_3$ is H or alkyl of 1 to 10 carbon atoms;

$R_4$ and $R_5$ are same or different and are hydrogen; alkanoyl of 2 to 21 carbon atoms; benzoyl, naphthoyl-1 or naphthoyl-2 each optionally substituted by halogen, alkyl of 1 to 3 carbon atoms, alkoxy of 1 to 3 carbon atoms, trifluoromethyl, hydroxy or alkanoyloxy of 1 to 3 carbons; and alkanesulfonic acid of 1 to 7 carbon atoms, or a phenylsulfonic acid optionally substituted by alkyl of 1 to 3 carbon atoms; carbamoyl, alkyl carbamoyl of 1 to 3 carbon atoms, phenylcarbamoyl or napththylcarbamoyl;

$R_6$ is H or $R_6$-$R_7$ together if —$CH_2$—$CH_2$—$CH_2$—;

$R_7$ is H, alkyl of 1 to 7 carbon atoms, hydroxymethyl, mercaptomethyl, benzyl; or substituted benzyl wherein the substituents are the same as defined for $R_1$;

$R_8$ and $R_9$ each is carboxyl, esterified carboxyl of 1 to 7 carbon atoms, amidated carboxyl, or mono- or dialkyl amidated carboxyl wherein the alkyl group has 1 to 3 carbon atoms; provided that when $R_3$ is lower alkyl, the stereochemistry at asymmetric center I can be either D or L, but that when the aminoglycose has the 2-amino-2-deoxy-D-glucose configuration, the stereochemistry at I cannot be D; when $R_7$ is not H, the stereochemistry at a symmetric center II is either L or D; and the stereochemistry at asymmetric center III is D; or pharmaceutically acceptable acid addition salts thereof; and an anti-viral, anti-AIDS drug selected from the group consisting of azidothymidine, ansamycin, ribavirin, deoxyytidine, HPA-23, AL-721, and foscarnet; in a physiologically acceptable medium in an amount effective to impart resistance against opportunistic bacterial, fungal or viral infection.

2. The composition according to claim 1 wherein the $R_1$ to $R_2$ alkyl group is optionally substituted by hydroxy, mercapto, or hydroxy or mercapto each substituted by an alkyl group of 1 to 3 carbon atoms, and wherein the $R_1$ and $R_2$ phenyl group and the $R_1$ benzyl group are optionally substituted by an alkyl group of 1 to 3 carbon atoms, hydroxy, mercapto, amino, trifluoromethyl, alkyldioxy of 1 to 4 carbon atoms, cycloalkyldioxy of 5 to 7 carbon atoms, hydroxy or mercapto etherified by an alkyl group of 1 to 3 carbon atoms, or hydroxy or mercapto esterified by an acid of 1 to 4 carbon atoms.

3. The composition of claim 1 wherein $R_1$ is H, alkyl of 1 to 3 carbon atoms, benzyl, phenyl or phenyl p-substituted by alkyl (1 to 3 carbon atoms), amino, halogen, hydroxy or trifluoromethyl;

$R_2$ is alkyl of 1 to 3 carbon atoms, or phenyl, or phenyl p-substituted by alkyl (1 to 3 carbon atoms), amino, halogen, hydroxy or trifluoromethyl;

$R_3$ is H or lower alkyl 1 to 3 carbon atoms;

$R_4$ and $R_5$ are H, alkanoyl of 2 to 21 carbon atoms, benzoyl or naphthoyl;

$R_7$ is H, alkyl of 1 to 4 carbon atoms, hydroxymethyl, mercaptomethyl, benzyl or $R_6$ and $R_7$ together are —$CH_2CH_2CH_2$—, and $R_8$ and $R_9$ are carboxyl, carboxyl esterified by an alcohol of 1 to 4 carbon atoms, carboxamide or monoalkyl or dialkyl substituted carboxamide wherein the alkyl group has from 1 to 3 carbon atoms.

4. A method for enhancing host resistance against opprotunistic bacterial, fungal or viral infection in a human host immunocompromised by an AIDS related virus comprising the step of administering to said host a composition comprising a compound according to claim 1.

* * * * *